United States Patent
Chard et al.

(10) Patent No.: US 10,232,365 B2
(45) Date of Patent: Mar. 19, 2019

(54) TEST DEVICE AND SAMPLE CARRIER

(71) Applicant: AgPlus Diagnostics Ltd, Hook, Hampshire (GB)

(72) Inventors: Michael Chard, Hook (GB); Robert Porter, Hook (GB); Courtney Nicholson, Hook (GB); Andrew Lakey, Hook (GB); Simon Attree, Hook (GB); Philip Walsh, Bristol (GB); Philip Potter, Bristol (GB); Craig Wightman, Bristol (GB); Paul Dyckes, Newport (GB); Holger Becker, Jena (DE); Rene Stewart, Jena (DE); Wolfgang Engelhart, Jena (DE); Claudia Gaertner, Jena (DE)

(73) Assignee: AGPLUS DIAGNOSTICS LTD, Hampshire (GB)

( * ) Notice: Subject to any disclaimer, the term of this patent is extended or adjusted under 35 U.S.C. 154(b) by 862 days.

(21) Appl. No.: 14/432,139

(22) PCT Filed: Sep. 27, 2013

(86) PCT No.: PCT/GB2013/052529
§ 371 (c)(1),
(2) Date: Mar. 27, 2015

(87) PCT Pub. No.: WO2014/049371
PCT Pub. Date: Apr. 3, 2014

(65) Prior Publication Data
US 2015/0298118 A1    Oct. 22, 2015

(30) Foreign Application Priority Data
Sep. 28, 2012 (GB) .................................. 1217390.2

(51) Int. Cl.
*G01N 33/53* (2006.01)
*F16K 7/06* (2006.01)
(Continued)

(52) U.S. Cl.
CPC .......... *B01L 3/502* (2013.01); *B01L 3/50273* (2013.01); *B01L 9/52* (2013.01); *B01L 9/527* (2013.01);
(Continued)

(58) Field of Classification Search
None
See application file for complete search history.

(56) References Cited

U.S. PATENT DOCUMENTS

| 4,628,169 A | 12/1986 | Ch'ing-Lung |
| 5,096,669 A | 3/1992 | Lauks et al. |

(Continued)

FOREIGN PATENT DOCUMENTS

| EP | 0374439 | 6/1990 |
| EP | 1400600 | 3/2004 |

(Continued)

OTHER PUBLICATIONS

Dequaire et al. (2000) "An Electrochemical Melalloimmunoassay Based on a Colloidal Gold Label" *Anal. Chem*; 72:5521-5528.
(Continued)

*Primary Examiner* — Christopher L Chin
(74) *Attorney, Agent, or Firm* — Edward J. Baba; Bozicevic, Field & Francis LLP

(57) ABSTRACT

A test device (80) for testing for the presence of a substance in a sample held on a sample carrier (30) includes a holder (82) for holding a sample carrier (30) which includes one or more chambers (50,52). The test device (80) also includes an actuator for compressing or depressurizing the chamber(s) (50,52). The actuator is configured to prevent reinflation of (Continued)

the chamber(s) (50,52) after compression or depressurization.

19 Claims, 32 Drawing Sheets

(51) Int. Cl.
*B01L 9/00* (2006.01)
*B01L 3/00* (2006.01)
*G01N 33/558* (2006.01)

(52) U.S. Cl.
CPC ............... *F16K 7/06* (2013.01); *B01L 3/545* (2013.01); *B01L 2200/025* (2013.01); *B01L 2200/027* (2013.01); *B01L 2200/0621* (2013.01); *B01L 2200/0647* (2013.01); *B01L 2200/0684* (2013.01); *B01L 2200/10* (2013.01); *B01L 2200/16* (2013.01); *B01L 2300/021* (2013.01); *B01L 2300/027* (2013.01); *B01L 2300/044* (2013.01); *B01L 2300/045* (2013.01); *B01L 2300/06* (2013.01); *B01L 2300/0609* (2013.01); *B01L 2300/0645* (2013.01); *B01L 2300/0672* (2013.01); *B01L 2300/0816* (2013.01); *B01L 2300/0867* (2013.01); *B01L 2400/043* (2013.01); *B01L 2400/049* (2013.01); *B01L 2400/0481* (2013.01); *B01L 2400/086* (2013.01); *G01N 33/5302* (2013.01)

(56) References Cited

U.S. PATENT DOCUMENTS

| | | | |
|---|---|---|---|
| 5,710,404 | A | 1/1998 | Descent |
| 5,835,329 | A | 11/1998 | Sucholeiki |
| 5,863,502 | A | 1/1999 | Southgate et al. |
| 6,159,739 | A | 12/2000 | Weigl et al. |
| 6,159,747 | A | 12/2000 | Harttig et al. |
| 6,300,141 | B1 | 10/2001 | Segal et al. |
| 6,319,469 | B1 | 11/2001 | Mian et al. |
| 6,326,612 | B1 | 12/2001 | Elkind et al. |
| 6,548,311 | B1 | 4/2003 | Knoll |
| 6,750,053 | B1 | 6/2004 | Widrig et al. |
| 6,975,395 | B1 | 12/2005 | Gentieu et al. |
| 7,045,364 | B2 | 5/2006 | Limoges et al. |
| 7,226,562 | B2 | 6/2007 | Holl et al. |
| 7,419,821 | B2 | 9/2008 | Davis et al. |
| 7,745,228 | B2 | 6/2010 | Schwind et al. |
| 8,017,382 | B2 | 9/2011 | Davis et al. |
| 8,222,024 | B2 | 7/2012 | Davis et al. |
| 8,337,692 | B2 | 12/2012 | Porter et al. |
| 8,445,293 | B2 | 5/2013 | Babu et al. |
| 8,507,260 | B2 | 8/2013 | Alajem et al. |
| 8,927,299 | B2 | 1/2015 | Porter |
| 2001/0035955 | A1 | 11/2001 | Ruevski et al. |
| 2002/0137218 | A1 | 9/2002 | Mian et al. |
| 2002/0197733 | A1 | 12/2002 | Bohm et al. |
| 2003/0178641 | A1 | 9/2003 | Blair et al. |
| 2003/0186274 | A1 | 10/2003 | Limoges et al. |
| 2004/0028566 | A1 | 2/2004 | Ko et al. |
| 2004/0058457 | A1 | 3/2004 | Huang et al. |
| 2004/0132220 | A1 | 7/2004 | Fish |
| 2004/0215225 | A1 | 10/2004 | Nakayama |
| 2004/0248093 | A1 | 12/2004 | Coombs et al. |
| 2005/0026346 | A1 | 2/2005 | Blankenstein et al. |
| 2005/0230713 | A1 | 10/2005 | Brousseau, III |
| 2006/0000710 | A1 | 1/2006 | Weidenhaupt et al. |
| 2006/0228814 | A1 | 10/2006 | Limoges et al. |
| 2006/0263818 | A1 | 11/2006 | Scherer et al. |
| 2006/0270049 | A1 | 11/2006 | Todd |
| 2007/0148039 | A1 | 6/2007 | Padmanabhan et al. |
| 2007/0149897 | A1 | 6/2007 | Ghesquiere et al. |
| 2007/0202561 | A1 | 8/2007 | Rosenstein et al. |
| 2009/0159458 | A1 | 6/2009 | Tamiya |
| 2010/0034742 | A1 | 2/2010 | Schwartz et al. |
| 2011/0124008 | A1 | 5/2011 | Nam et al. |
| 2011/0171735 | A1 | 7/2011 | Porter |
| 2012/0167672 | A1 | 7/2012 | Miller |
| 2014/0251832 | A1 | 9/2014 | Porter |

FOREIGN PATENT DOCUMENTS

| | | |
|---|---|---|
| EP | 1481246 | 12/2004 |
| EP | 1611836 | 1/2006 |
| FR | 2618336 | 1/1989 |
| JP | 11322619 | 11/1999 |
| JP | 2000300664 | 10/2000 |
| JP | 2004195584 | 7/2004 |
| JP | 2004279179 | 10/2004 |
| JP | 2006153562 | 6/2006 |
| JP | 2007514142 | 5/2007 |
| JP | 2008051973 | 3/2008 |
| JP | 2010508039 | 3/2010 |
| JP | 2012517595 | 8/2012 |
| TW | 200422608 | 1/2004 |
| WO | WO 1990002938 | 3/1990 |
| WO | WO 1998028623 | 7/1998 |
| WO | 1998035225 | 8/1998 |
| WO | 1998038510 | 9/1998 |
| WO | WO 1998053301 | 11/1998 |
| WO | WO 1999022236 | 5/1999 |
| WO | WO 1999038612 | 8/1999 |
| WO | 2000005582 | 2/2000 |
| WO | 2000013715 | 3/2000 |
| WO | WO 2000013014 | 3/2000 |
| WO | WO 2000025136 | 5/2000 |
| WO | 2000050172 | 8/2000 |
| WO | WO 2000079276 | 12/2000 |
| WO | WO 2001067079 | 9/2001 |
| WO | 2002096592 | 12/2002 |
| WO | WO 2003076937 | 9/2003 |
| WO | WO 2004016160 | 2/2004 |
| WO | WO 2004020112 | 3/2004 |
| WO | WO 2004061418 | 7/2004 |
| WO | WO 2004113919 | 12/2004 |
| WO | WO 2005026178 | 3/2005 |
| WO | WO 2005046437 | 5/2005 |
| WO | WO 2005064349 | 7/2005 |
| WO | WO 2005121792 | 12/2005 |
| WO | 2006014524 | 2/2006 |
| WO | 2006036757 | 4/2006 |
| WO | WO 2006065762 | 6/2006 |
| WO | WO 2006104695 | 10/2006 |
| WO | WO 2006105110 | 10/2006 |
| WO | WO 2006118420 | 11/2006 |
| WO | WO 2007110779 | 10/2007 |
| WO | WO 2008002462 | 1/2008 |
| WO | WO 2008010058 | 1/2008 |
| WO | WO 2008055915 | 5/2008 |
| WO | WO 2008074146 | 6/2008 |
| WO | 2010004246 | 1/2010 |
| WO | WO 2010004244 | 1/2010 |
| WO | WO 2010091246 | 8/2010 |
| WO | WO 2011075667 | 6/2011 |
| WO | WO 2011100708 | 8/2011 |
| WO | WO 2011123064 | 10/2011 |
| WO | WO 2012045753 | 4/2012 |
| WO | WO 2012092010 | 7/2012 |
| WO | WO 2012092011 | 7/2012 |

OTHER PUBLICATIONS

Dianping et al. (2006) "Direct Electrochemical Immunassay Based on Immobilization of Protein-Magnetic Nanoparticle Composites on to Magnetic Electrode Surfaces by Sterically Enhanced Magnetic Field Force," *Biotechnology Letters*; 28(8):559-565.

Fritzsche and Talon (2003) "Metal nanoparticles as labels for heterogeneous, chip-based DNA detection," *Nanotechnology*; 14:R63-R73.

Guo and Wang (2007) "Synthesis and electrochemical applications of gold nanoparticles," *Analytica Chimica Acta*; 598:181-92.

(56) References Cited

OTHER PUBLICATIONS

Kim et al. (2006) "Superparamagnetic Nanoparticle-Based Nanobiomolecular Detection in a Microfluidic Channel," *Current Applied Physics*; 6(6):976-981.

Mandal et al. (2005) "Magnetite nanoparticles with tunable gold or silver shell," *Journal of Colloid and Interface Science*; 286(1):187-194.

Wang et al. (1999) "Spectroscopic studies of thiocyanate in silver hydrosol and the influence of halide ions," *Spectrochimica Acta Part A*; 55:991-998.

Yang et al. (2007) "Determination of trace thiocyanate with nano-silver coated multi-walled carbon nanotubes modified glassy carbon electrode," *Analytica Chimica Acta*; 585:331-336.

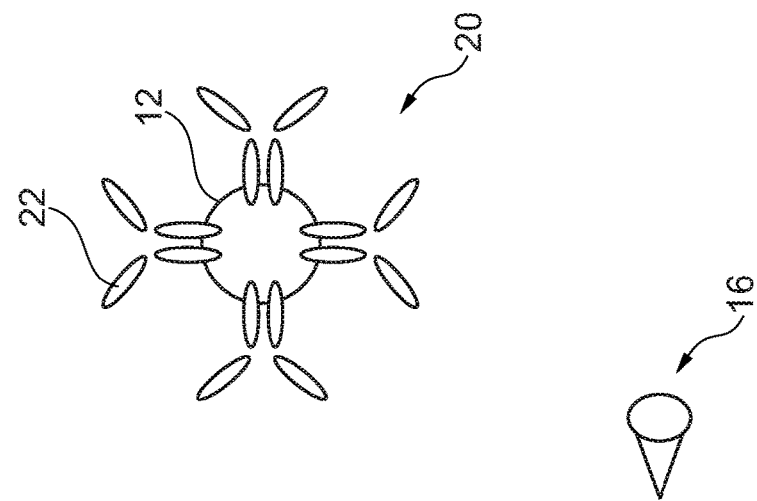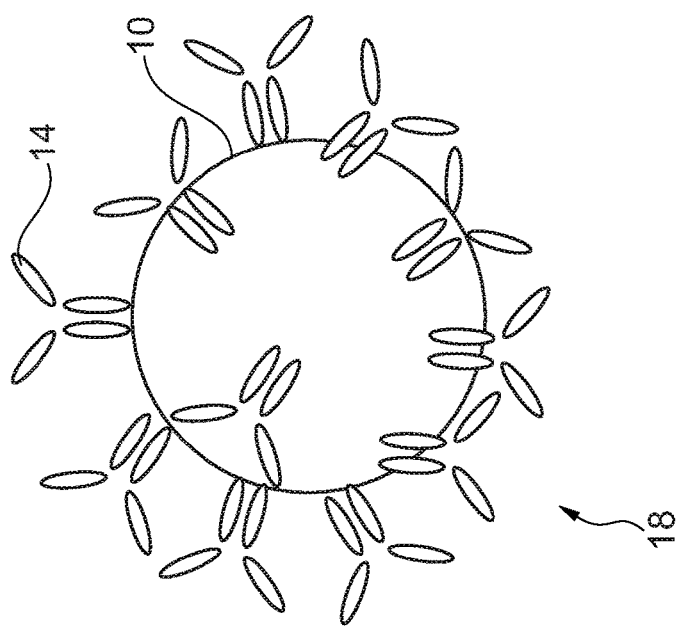
Fig. 1

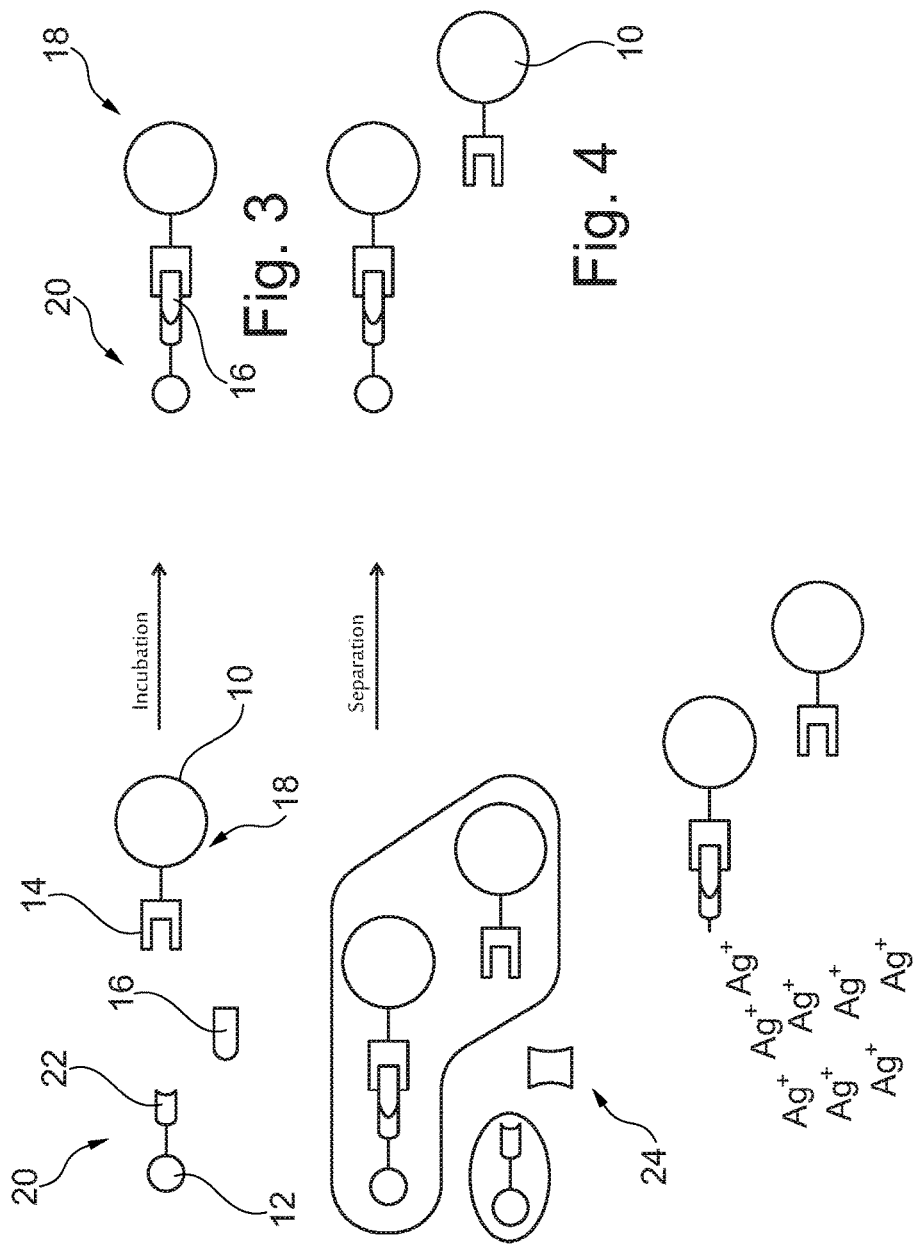

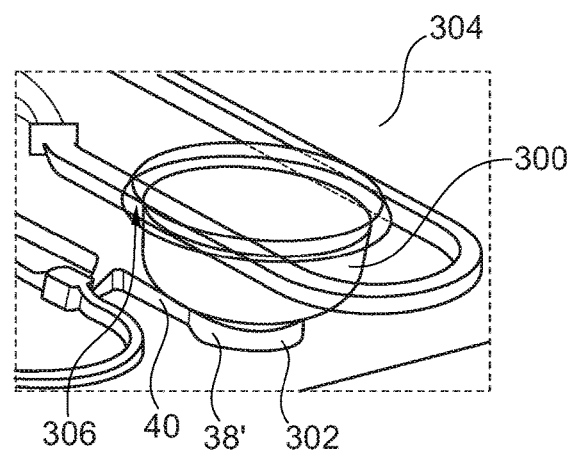
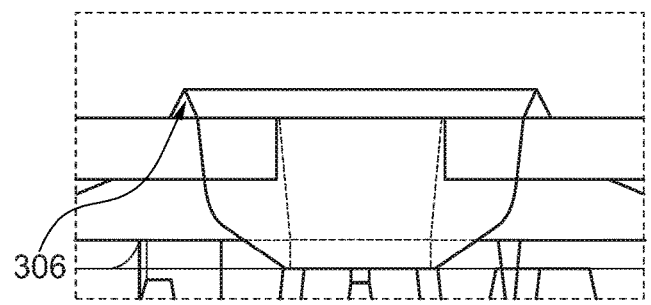
Fig. 14
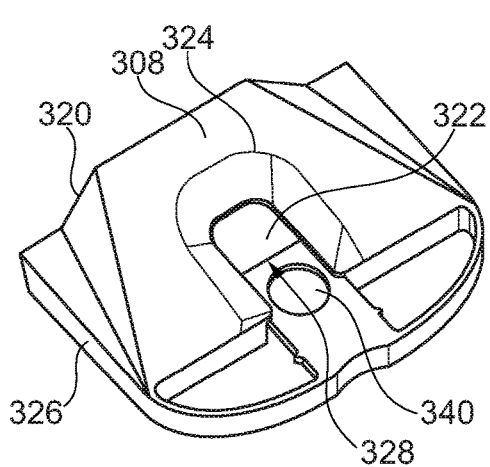
Fig. 15
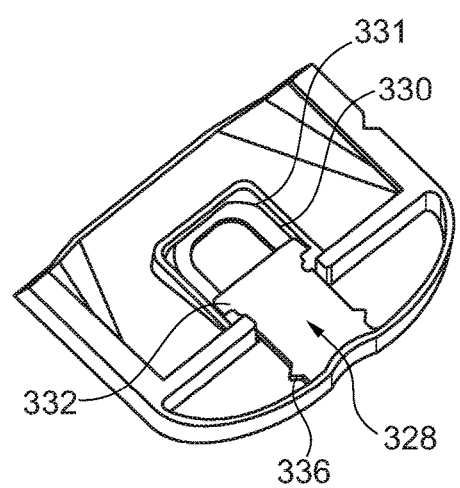
Fig. 16

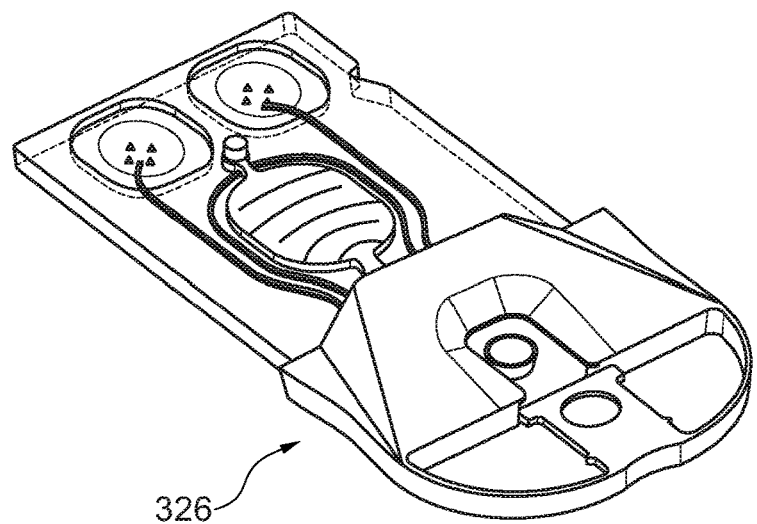
Fig. 22
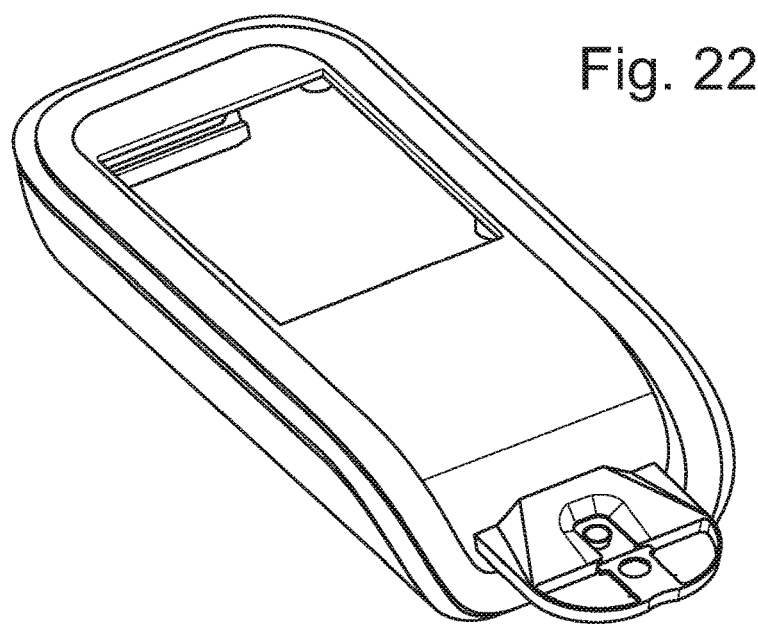
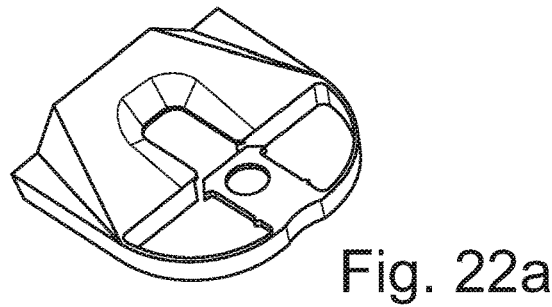
Fig. 22a

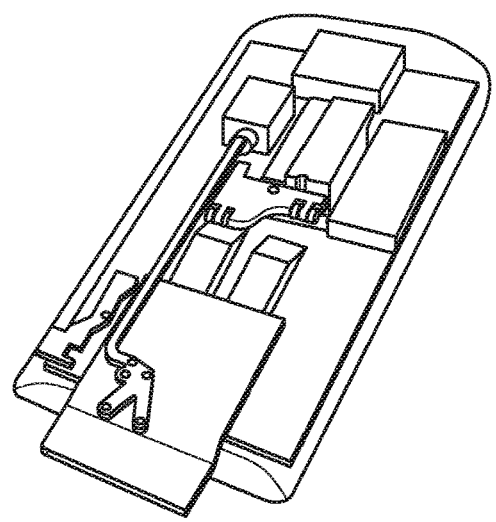
Fig. 33
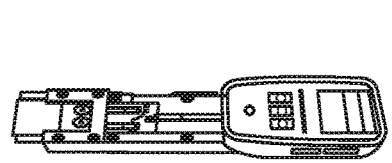
A
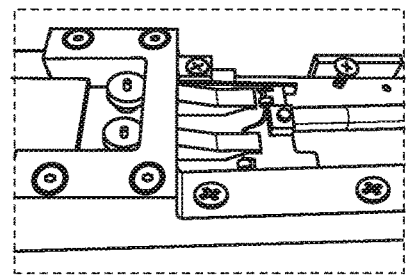
B
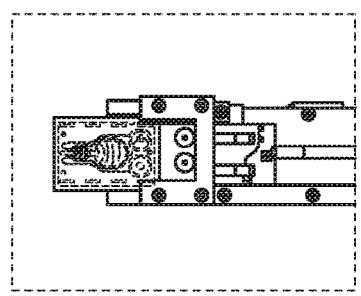
C
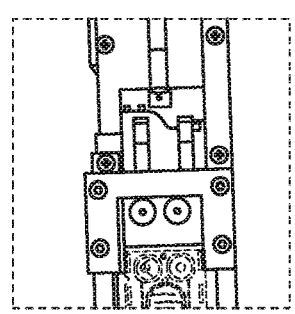
D
Fig. 34

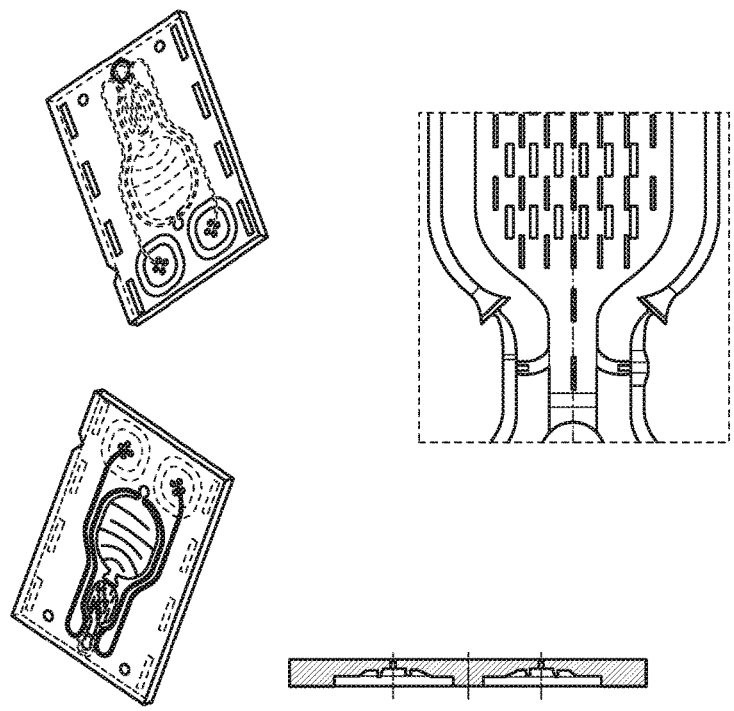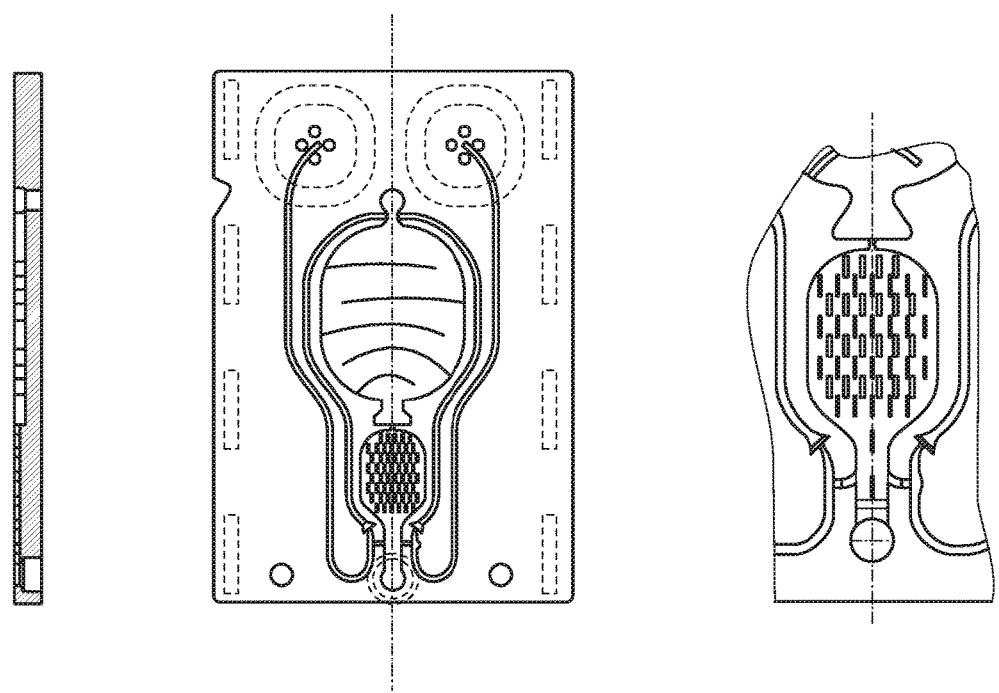
Fig. 40

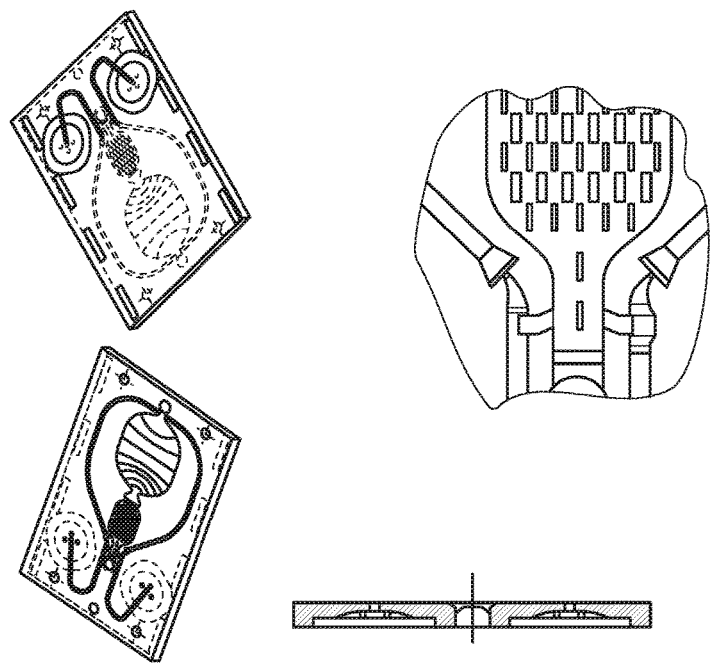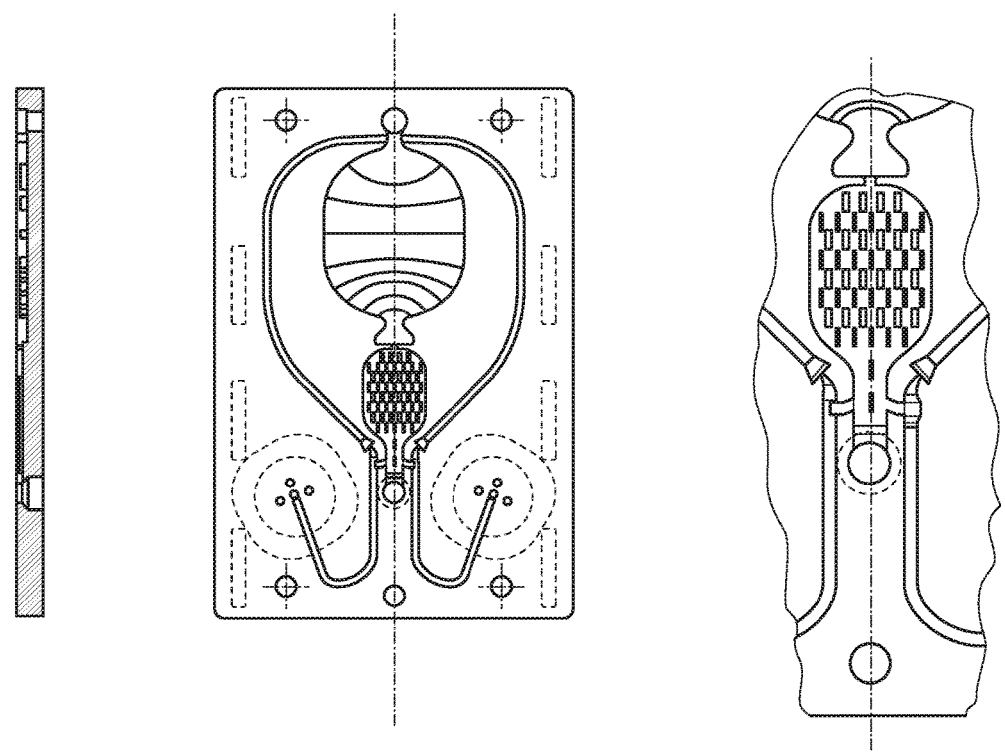
Fig. 44

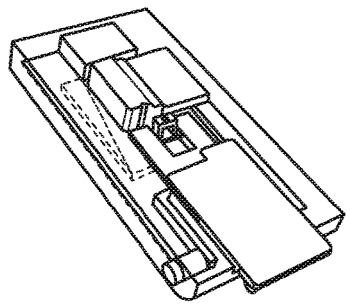
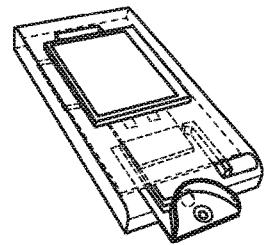
Fig. 48    Fig. 49
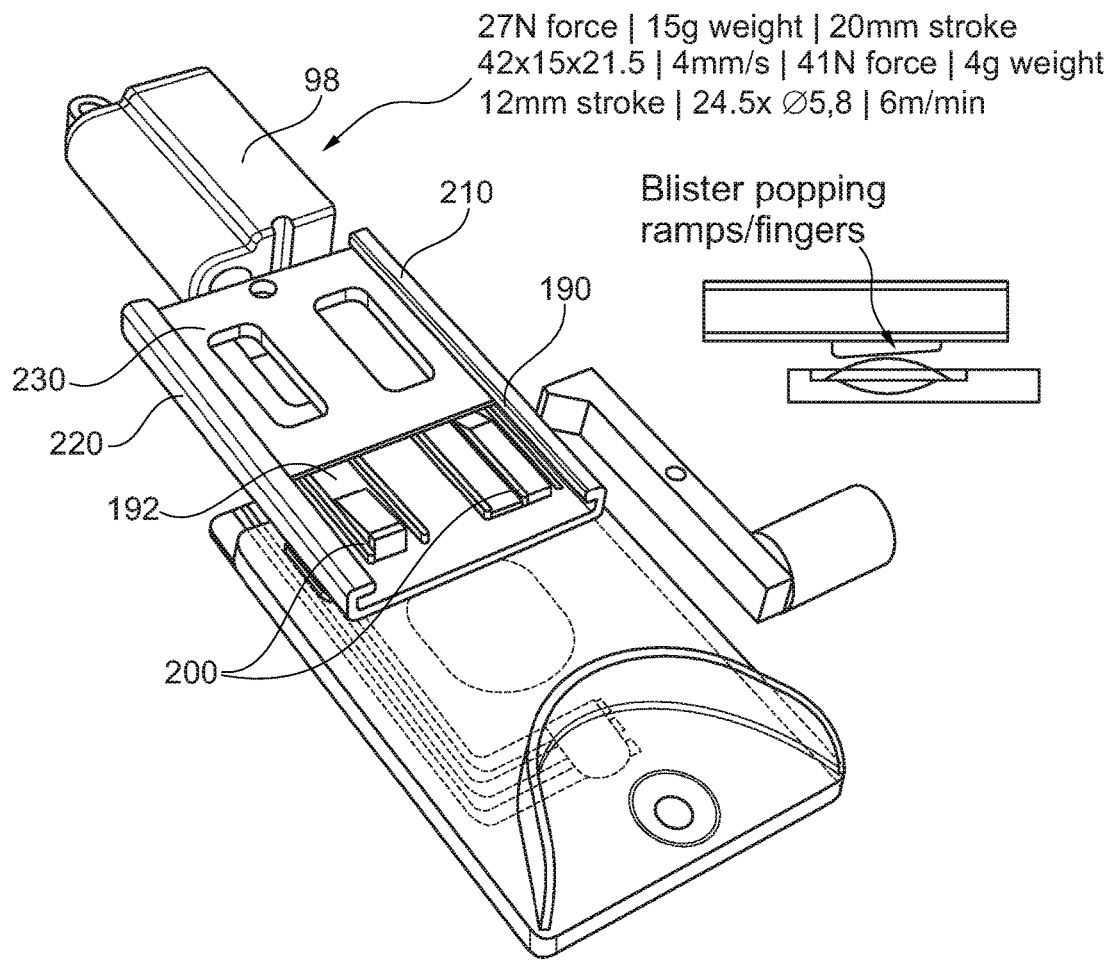
27N force | 15g weight | 20mm stroke
42x15x21.5 | 4mm/s | 41N force | 4g weight
12mm stroke | 24.5x ⌀5,8 | 6m/min
Blister popping ramps/fingers
Fig. 47

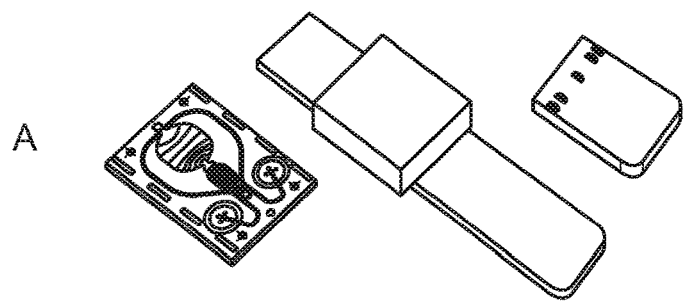
A
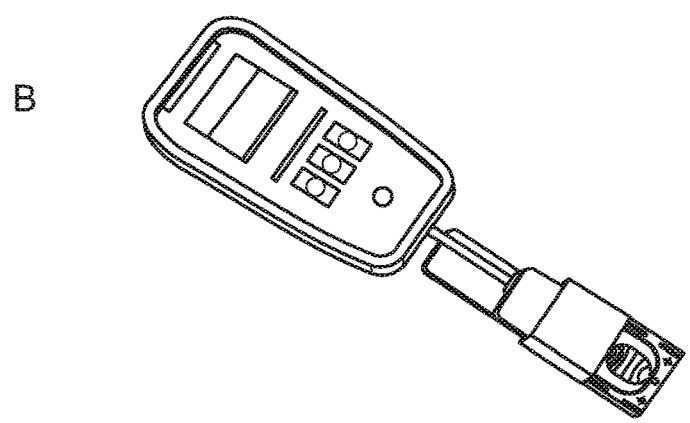
B
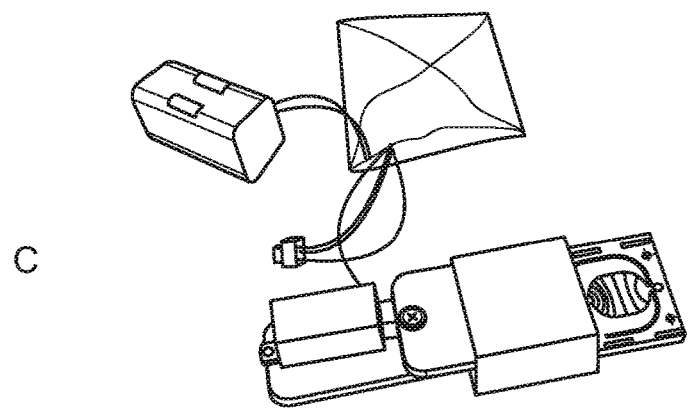
C
Fig. 50

TEST DEVICE AND SAMPLE CARRIER

The present invention relates to sample carriers and test devices therefor, for example to a chip and meter for an immunoassay.

Aspects of the present invention seek to provide an improved test device or sample carrier or at least provide a useful alternative to existing technology.

According to an aspect of the invention there is provided a test device for testing for the presence of a substance in a sample held on a sample carrier that includes a chamber or a plurality of chambers; the test device including a holder for holding a said sample carrier, and an actuator for compressing or depressurising a said chamber or a said plurality of chambers, wherein the actuator is configured to prevent reinflation of a said chamber or a said plurality of chambers after compression or depressurisation.

In embodiments, the chambers are compressible or pressurised chambers, preferably storage chambers for the storage of fluid, preferably liquid, for use in a test. The storage chambers can be preloaded with fluid, or they can temporarily store fluid during a test. The storage chambers are preferably burstable blisters.

Air bubbles in a sample carrier can interfere with a test. They can be located near to a detection element, which can cause erroneous test readings. Also, they can take up space within the sample carrier which should ideally be filled with sample. This can reduce the amount of sample in the sample carrier, potentially reducing the effectiveness of the test. Preferred embodiments of the invention, by preventing reinflation of the chambers once they have been compressed or depressurised, is able to prevent fluid from being sucked back away from other parts of the sample carrier in which it is needed. This in turn prevents air from being drawn into the sample carrier to replace the fluid being sucked back. It is also able to prevent storage chambers becoming inflated with air which may then diffuse or be drawn into other parts of the sample carrier.

Preferably, the actuator is operable to burst a said chamber or a said plurality of chambers. This enables the chamber(s) to be provided as sealed fluid-containing pouches or blisters, preventing early release of fluid before the blisters are burst.

Preferably, the test device is configured as part of a test to perform at least one interaction with a said sample carrier subsequently to compressing or depressurising a said chamber or a said plurality of chambers; the actuator being configured to prevent reinflation of a said chamber or a said plurality of chambers after compression or depressurisation, until at least a first of the at least one interaction has been performed, preferably until the or each of the at least one interaction has been performed. The sequence of interactions can include all interactions necessary for performing a test for the presence of a substance in a sample held on a said sample carrier.

Preferably, the actuator includes a first pivotable member including a first chamber actuation section pivotable into a first chamber location, wherein the first chamber location is a location at which a said chamber of a said sample carrier is located when a said sample carrier is held in the holder; and a driver operable to pivot the first pivotable member to cause the first chamber actuation section to be pivoted into the first chamber location thereby to compress or depressurise a said chamber in the first chamber location.

In embodiments, the actuator includes a second pivotable member including a second chamber actuation section pivotable into a second chamber location, wherein the second chamber location is a location at which a said chamber of a said sample carrier is located when a said sample carrier is held in the holder; the driver being operable to pivot the second pivotable member to cause the second chamber actuation section to be pivoted into the second chamber location thereby to compress or depressurise a said chamber in the second chamber location.

In preferred embodiments, using pivotable members has been found to be an effective way of providing a controlled compressing/depressurising force in a minimal space.

Preferably, the driver is configured to pivot the first pivotable member before the second pivotable member, preferably a predetermined period before. This can allow for chambers to be compressed/depressurised in a controlled sequence in order to effect the test being performed. Preferably, the predetermined period can be altered in dependence on the test being performed.

According to an aspect of the invention, there is provided a method of performing a test for a substance in a sample held in a sample carrier, including:
 operating an actuator to compress or depressurise a fluid-filled storage chamber of the sample carrier or a plurality of fluid-filled storage chambers of the sample carrier to cause fluid from the storage chamber or from the plurality of storage chambers to be moved;
 operating the actuator to prevent reinflation of the storage chamber or of the plurality of storage chambers;
 operating a detector to interact with fluid in the detection chamber to test for the substance.

Preferably, preventing reinflation of the storage chamber or of the plurality of storage chambers includes maintaining compression of the storage chamber or of the plurality of storage chambers.

Preferably, operating an actuator to compress or depressurise a fluid-filled storage chamber of the sample carrier or a plurality of fluid-filled storage chambers of the sample carrier causes fluid from the storage chamber or from the plurality of storage chambers to be moved into a detection chamber in which the sample is held, for example to provide part of the functionality of a test being performed. For example, the fluid from the storage chamber(s) can be wash fluid to wash unbound particles out of the detection chamber or detection fluid to cause a detectable reaction in the detection chamber.

The test device can be for performing an assay such as an electrochemical assay.

In embodiments, the detector includes an electrode.

In embodiments, the detection chamber is provided, for example preloaded, with reagents for performing a test. In some embodiments, the reagents include carrier elements and label elements for binding to an analyte. The carrier elements and label elements can be preloaded for example in a dried down form. The carrier elements can be magnetic.

According to an aspect of the invention, there is provided a sample carrier for use in testing for the presence of a substance in a sample, the sample carrier including: an inlet for receiving a sample to be tested; a detection chamber coupled to the inlet for receiving a sample from the inlet; a plurality of electrodes at least partially in the detection chamber; and a connector for electrically connecting the sample carrier to a test device; wherein each of the plurality of electrodes is coupled to the connector by a respective electrically conductive track on the sample carrier; wherein each of the tracks is configured to provide an electrical resistance between the respective electrode and the connector; wherein the resistances of each of the tracks are substantially equal.

It has been found that providing substantially parallel tracks with equal widths can provide erroneous readings. This has been discovered to be at least partially as a result of the tracks having different resistances. Preferred embodiments provide the tracks with equal resistances and thereby provide more reliable readings.

According to an aspect of the invention, there is provided a sample carrier for use in testing for the presence of a substance in a sample, the sample carrier having a proximal end and a distal end, the sample carrier including: an inlet for receiving a sample to be tested; a detection chamber coupled to the inlet; and at least one storage chamber coupled to the detection chamber, the at least one storage chamber being preloaded with a fluid and being compressible or being able to be depressurised to provide the preloaded fluid to the detection chamber; wherein the inlet is closer than the detection chamber to the proximal end of the sample carrier and the at least one storage chamber is closer than the detection chamber to the distal end of the sample carrier.

According to an aspect of the invention, there is provided a sample carrier for use in testing for the presence of a substance in a sample, the sample carrier including: an inlet for receiving a sample to be tested; a detection chamber coupled via a conduit to the inlet for receiving a sample from the inlet; and a test element for acting on a sample in the detection chamber to allow a substance to be detected; wherein the inlet includes a bowl for receiving a sample, the bowl having a volume corresponding to a volume of sample for providing an effective test in the sample carrier.

It is important that the sample carrier receives the correct amount of sample, since too little will leave air in the sample carrier which may have an adverse effect on readings, and too much may result in excess sample leaking out of the sample carrier, with consequential hazardous results. Preferred embodiments provide a convenient way of ensuring the optimum amount of sample is provided. Preferably, the volume of the bowl corresponds to a combined volume of the detection chamber and the conduit since this is the amount of sample which will fill the sample carrier sufficiently for an effective test.

Preferred embodiments include a closure member to close the bowl, thereby removing any sample in excess of the volume of the bowl.

Preferably, the detection chamber is coupled to a waste chamber via a valve. The valve and the closure member bound a fixed volume for sample. The valve can prevent migration of sample into the waste chamber and can prevent waste from moving back into the detection chamber.

Preferably, the closure member is configured to close the bowl in a substantially airtight manner, thereby ensuring that sample cannot leak out after the bowl has been closed. It also ensures that air cannot enter, which might otherwise cause erroneous readings.

Preferably, the closure member is movable in a guide to close the bowl, wherein a thickest section of the closure member is thicker than a section of the guide member where the thickest section of the closure member is located in a closed position, thereby to force the closure member against an edge of the bowl in the closed position to form an airtight seal.

Preferably, the closure member includes a closure protrusion configured to enter and close an opening of the bowl in the closed position.

The closure protrusion may be provided with a membrane overmoulding on a side opposite a side which is configured to be positioned adjacent to the bowl in the closed position, thereby to provide an increased effectiveness to the seal.

According to an aspect of the invention, there is provided a sample carrier for use in testing for the presence of a substance in a sample, the sample carrier including: an inlet for receiving a sample to be tested; a detection chamber coupled to the inlet; and at least one storage chamber coupled to the detection chamber, the at least one storage chamber being preloaded with a fluid and being compressible or being able to be depressurised to move the preloaded fluid from the at least one storage chamber to another part of the sample carrier; wherein the or each of the at least one storage chamber includes a blister positioned adjacent to a recess such that pressure on the blister causes the blister to be pushed into the recess, an edge of the recess having a curved shoulder and the recess including one or more pins to puncture and burst the blister.

Preferred embodiments utilised the curved should to maximise the amount of fluid drawn from the blister and to minimise air entering the sample carrier.

According to an aspect of the invention there is provided a sample carrier for use in testing for the presence of a substance in a sample, the sample carrier including: an inlet for receiving a sample to be tested; a detection chamber coupled via a conduit to the inlet for receiving a sample from the inlet; and a test element for acting on a sample in the detection chamber to allow a substance to be detected; wherein the detection chamber is substantially hexagonal.

It has been found that a hexagonal detection chamber minimises air bubbles being trapped in the detection chamber, which might otherwise cause erroneous readings.

According to an aspect of the invention there is provided a sample carrier for use in testing for the presence of a substance in a sample, the sample carrier including: an inlet for receiving a sample to be tested; a detection chamber coupled via a conduit to the inlet for receiving a sample from the inlet; and a test element for acting on a sample in the detection chamber to allow a substance to be detected; wherein the detection chamber includes a plurality of projections to provide surface area to aid mixing in the detection chamber.

The plurality of projections can include a plurality of pillars.

According to an aspect of the invention, there is provided a sample carrier for use in testing for the presence of a substance in a sample, the sample carrier having a proximal end and a distal end, the sample carrier including: an inlet for receiving a sample to be tested; a detection chamber coupled to the inlet, the detection chamber being for use in performing an assay; and at least one storage chamber coupled to the detection chamber, the at least one storage chamber being preloaded with a fluid and being compressible to provide the preloaded fluid to the detection chamber; wherein the inlet is closer than the detection chamber to the proximal end of the sample carrier and the at least one storage chamber is closer than the detection chamber to the distal end of the sample carrier.

According to an aspect of the invention, there is provided a sample carrier for use in testing for the presence of a substance in a sample, the sample carrier having a proximal end and a distal end, the sample carrier including: an inlet for receiving a sample to be tested; a detection chamber coupled to the inlet, the detection chamber being preloaded with carrier elements and label elements for use in performing an assay; and at least one storage chamber coupled to the detection chamber, the at least one storage chamber including a first chamber preloaded with a detection solution and being compressible to provide the detection solution to the detection chamber; wherein the inlet is closer than the detection chamber to the proximal end of the sample carrier and the at least one storage chamber is closer than the detection chamber to the distal end of the sample carrier.

In other words, the sample carrier includes no compressible chamber or pressurised chamber configured to be depressurised which is closer than the detection chamber to the proximal end of the sample carrier.

A compressible chamber is one which is designed to be compressed as part of the operation of the sample carrier in order to move sample or fluids within the sample carrier.

In many prior art arrangements, a blister was located in the vicinity of test components. In general, this meant that the sample to be tested needed to be input before the sample carrier was inserted into a test device. This was because the sample carrier needed to be inserted into the test device sufficiently far so that the blister could in fact be burst by components within the test device. In embodiments of the present invention, the inlet can extend out of the test device while the sample carrier is held in a holder of the test device because the compressible chambers are located towards the distal end of the sample carrier. Furthermore, this can be achieved without requiring an overly long inlet channel. An overly long inlet channel can mean that a large amount of sample is required in order to fill the channel, and this can prolong the length of time needed to make an assay.

Therefore, embodiments of the present invention can enable the sample carrier to be held in the test device before the sample is added to the inlet while minimising the amount of sample that is required to be input into the sample carrier, thereby minimising the length of time for performing an assay.

It can be particularly advantageous to be able to insert the sample carrier into the test device before adding the sample for example to enable a user to confirm that the sample carrier is the correct sample carrier for the assay he or she wishes to perform. For example the test device may be provided with a reader which can read an identification code from the sample carrier and display on a screen information relating to which test the sample carrier can perform.

Preferably, the point of the first storage chamber which is closest to the proximal end of the sample carrier is closer to the distal end of the sample carrier than is the point of the detection chamber which is closest to the distal end of the sample carrier.

Preferably, there is no part of a compressible chamber which is closer to the proximal end of the sample carrier than is the point of the detection chamber which is closest to the distal end of the sample carrier.

In some embodiments, the at least one storage chamber includes a second storage chamber coupled to the detection chamber, wherein the second storage chamber is preloaded with a wash solution, is compressible to provide wash solution to the detection chamber, and is closer than the detection chamber to the distal end of the sample carrier. Preferably the point of the second storage chamber which is closest to the proximal end of the sample carrier is closer to the distal end of the sample carrier than is the point of the detection chamber which is closest to the distal end of the sample carrier.

In some embodiments, the first storage chamber and/or the second storage chamber and/or any other storage chambers each include a blister positioned over one or more pins so that compression of the blister causes the blister to be punctured and burst by the one or more pins.

According to an aspect of the invention, there is provided a test device for testing for the presence of a substance in a sample held on a sample carrier that includes a plurality of fluid-filled blisters; the test device including a holder for holding a sample carrier, and an actuator for compressing and busting the plurality of fluid-filled blisters in a controlled sequence.

According to an aspect of the invention, there is provided a test device for testing for the presence of a substance in a sample held on a sample carrier, the test device including a holder for holding a sample carrier, and an actuator; the actuator including a first pivotable member including a first chamber actuation section disposed above a first chamber location, wherein the first chamber location is a location at which a compressible chamber of a sample carrier is located when a sample carrier is held in the holder; the actuator further including a driver operable to pivot the first pivotable member to cause the first chamber actuation section to be pivoted into the first chamber location thereby to compress a compressible chamber in the first chamber location.

Embodiments of the invention provide the advantage that compressible chambers of a sample carrier can be actuated by a pivotable member. The pivotable member is able to provide consistent and reliable strength and direction of force.

According to an aspect of the invention, there is provided a test device for testing for the presence of a substance in a sample held on a sample carrier that includes at least one compressible chamber; the test device including a holder for holding a sample carrier, and an actuator for compressing at least one compressible chamber on a sample carrier held in the holder; wherein the holder is configured to allow the insertion of a sample carrier with the at least one compressible chamber uncompressed.

In other words, the holder is configured to allow the insertion of a sample carrier into the holder without compression or depressurisation of any storage chambers on the sample carrier.

In many prior art devices, the process of inserting a disposable device into a reader caused a mechanical action to be performed on the disposable device. This could mean that at least the beginning of the test sequence was not carefully controlled since the timings of the initial stages were affected by the speed and force with which the disposable device was inserted into the reader. Embodiments of the invention are able to reduce or overcome this problem by providing a holder which avoids any compression of compressible chambers during insertion. After insertion, the test device of embodiments of the invention can begin a carefully controlled sequence of steps to perform an assay.

The actuator can include a first pivotable member including a first chamber actuation section disposed above a first chamber location, wherein the first chamber location is a location at which a compressible chamber of a sample carrier is located when a sample carrier is held in the holder; and the actuator can include a driver operable to pivot the first pivotable member to cause the first chamber actuation section to be pivoted into the first chamber location whereby to compress a compressible chamber in the first chamber location.

In some embodiments, the first pivotable member also includes a second chamber actuation section disposed above a second chamber location, wherein the second chamber location is a location at which a compressible chamber of a sample carrier is located when a sample carrier is held in the holder. In these embodiments, the driver is operable to pivot the first pivotable member to cause the second chamber actuation section to be pivoted into the second chamber location whereby to compress a compressible chamber in the second chamber location.

In some embodiments, the driver is operable to pivot the first pivotable member to cause the first chamber actuation section to be pivoted into the first chamber location a predetermined period before pivoting the second chamber actuation section into the second chamber location.

In some embodiments, the actuator includes a second pivotable member including a second chamber actuation section disposed above a second chamber location, wherein the second chamber location is a location at which a compressible chamber of a sample carrier is located when a sample carrier is held in the holder. In these embodiments, the driver is operable to pivot the second pivotable member to cause the second chamber actuation section to be pivoted into the second chamber location whereby to compress a compressible chamber in the second chamber location.

In some embodiments, the driver is configured to pivot the first pivotable member before the second pivotable member, preferably a predetermined period before. In some embodiments, the predetermined period can be dependent upon the kind of test being performed.

Pivoting the first actuation section a predetermined period before the second actuation section enables embodiments of the invention to provide a carefully controlled delay between for example washing unbound label particles out of a detection zone of a sample carrier and detecting label elements in the detection zone. This can ensure that sufficient time is allowed to maximise removal of unbound label particles that might otherwise cause erroneous readings, while minimising the overall time for performing an assay.

In some embodiments the driver includes a linear motor operable to advance a pivot actuation member, wherein the pivot actuation member is configured to pivot the first pivotable member before the second pivotable member as it advances.

In some embodiments the driver includes a linear motor operable to advance a first pivot actuation member and a second pivot actuation member simultaneously, wherein the first pivot actuation member is longer than the second pivot actuation member whereby to pivot the first pivotable member before pivoting the second pivotable member as the first and second pivot actuation members advance.

In some embodiments, the linear motor is operable to advance the first pivot actuation member and the second pivot actuation member at the same speed.

In some embodiments, the first pivot actuation member and the second pivot actuation member are integral parts of a single pivot actuation member.

In some embodiments, the first and second pivotable members include a distal contact surface, and the pivot of each of the first and second pivotable members is arranged to be proximal of the distal contact surface and distal of the chamber actuation section; wherein the first and second pivot actuation members are configured to contact the distal contact surface of, respectively, the first and second pivotable members, as they are advanced by the linear motor.

In some embodiments, the distal contact surface of each of the first and second pivotable members is inclined with respect to the direction of advancement of the linear motor.

In some embodiments, the driver can be configured to allow a predetermined delay after insertion of a sample carrier into the test device before causing the compression of any compressible chambers on a sample carrier held in the test device. This can allow a predetermined incubation time for example for a sample to mix and bind with carrier and label elements in a chamber of the sample carrier.

In some embodiments, the driver is configured to begin the predetermined delay in response to an input from a user. This can enable a user to indicate to the test device when a sample has been inserted into the sample carrier before the test device begins calculating the incubation time.

According to an aspect of the invention, there is provided a combination of a test device as described above and a sample carrier as described above.

According to an aspect of the invention, there is provided a method of performing an assay, including:
   providing carrier elements and label elements in a detection chamber, wherein the carrier elements and label elements are configured to bind to an analyte of interest;
   inputting a sample to be tested into the detection chamber to allow the carrier elements and label elements to bind to any analytes of interest within the sample;
   holding the carrier elements and thereby the analytes of interest and the label elements which are bound to the analytes of interest in the detection chamber while applying a wash solution to remove from the detection chamber the remainder of the sample that is not bound to a carrier element;
   detecting the label elements in the detection chamber and thereby obtaining a reading relating to the number of analytes of interest in the sample.

In embodiments, the carrier elements are magnetic particles and the step of holding the carrier elements and thereby the analytes of interest and the label elements which are bound to the analytes of interest in the detection chamber includes applying an electromagnetic/magnetic field to the detection chamber.

In embodiments, detecting the label elements in the detection chamber includes applying a detection solution to the detection chamber and preferably taking readings using an electrode in the detection chamber.

Embodiments of the invention provide a metalloimmunoassay fluidic device that uses two blisters to be burst in sequence in a controlled manner. The device is retained in the meter for a fixed period of time before actuation of the first blister to allow for the sample to incubate with reagent in a measurement or detection chamber. After that incubation period a linear motor is activated, this drives forward a linear piston, which carries forward a chip actuation mechanism, which has bearing to help it move forwards smoothly. The actuation mechanism can be stepped so that one blister can be activated first, leaving the second blister un-burst until a later time when it is required to be burst. The actuation mechanism moves forward and underneath a CAM surface pushing up a rocker arm on that side of a pivot and pushing down a rocker arm on the other side of a pivot onto the blister thus bursting the blister. The linear motor will continue to move forward the other side of the actuation mechanism, which is stepped back, now come in contact with the second CAM surface and rocker arm. This forces up the second rocker arm on one side of a pivot and forces down the second rocker arm onto the second blister thus bursting it and delivering the liquid to the device.

The liquid in the first blister is used to wash any unbound metal nano-particle into the waste chamber and the second blister has a solution such as ammonium thiocyanate in to allow the release of the metal nano-particles to make them accessible and active to be read at an electrode.

Embodiments of the invention allow for the incubation of a sample in a meter and the ability to control the bursting of one blister and then a subsequent blister at a later date. This concept of bursting blisters in sequence could be extended to any number of blisters.

Although the embodiments described in detail herein relate to an electrical detection-based system, the use of many blisters burst in sequence can equally be applied to an optical based immunoassay fluidic device.

Preferred embodiments of the invention are described below, by way of example only, with reference to the accompanying drawings, in which:

FIG. 1 is a schematic diagram of various elements used in a test method in embodiments of the invention, including magnetic particles to which antibodies are attached, a silver sol particle to which one or more antibodies are attached and an antigen;

FIG. 3 is a schematic diagram of the first stage of the analysis procedure, termed an incubation stage;

FIG. 4 is a schematic diagram of a separation stage of the analysis procedure;

FIG. 5 shows the stage of the analysis procedure after dissolution of the silver sol particles;

Figure 6:
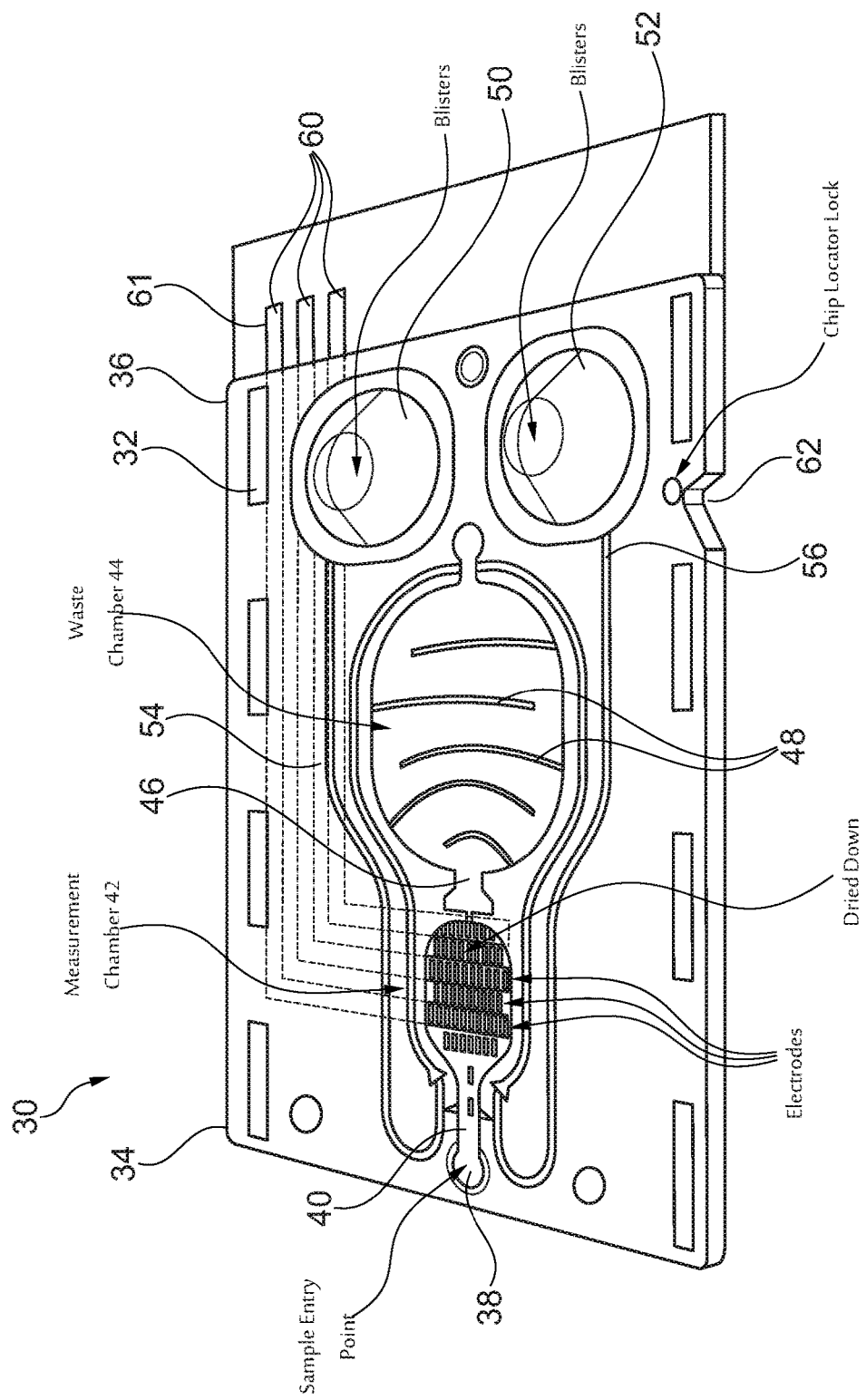
FIG. 6 is a perspective view of a sample carrier according to an embodiment of the invention in the form of a test strip or chip.
Figure 7:
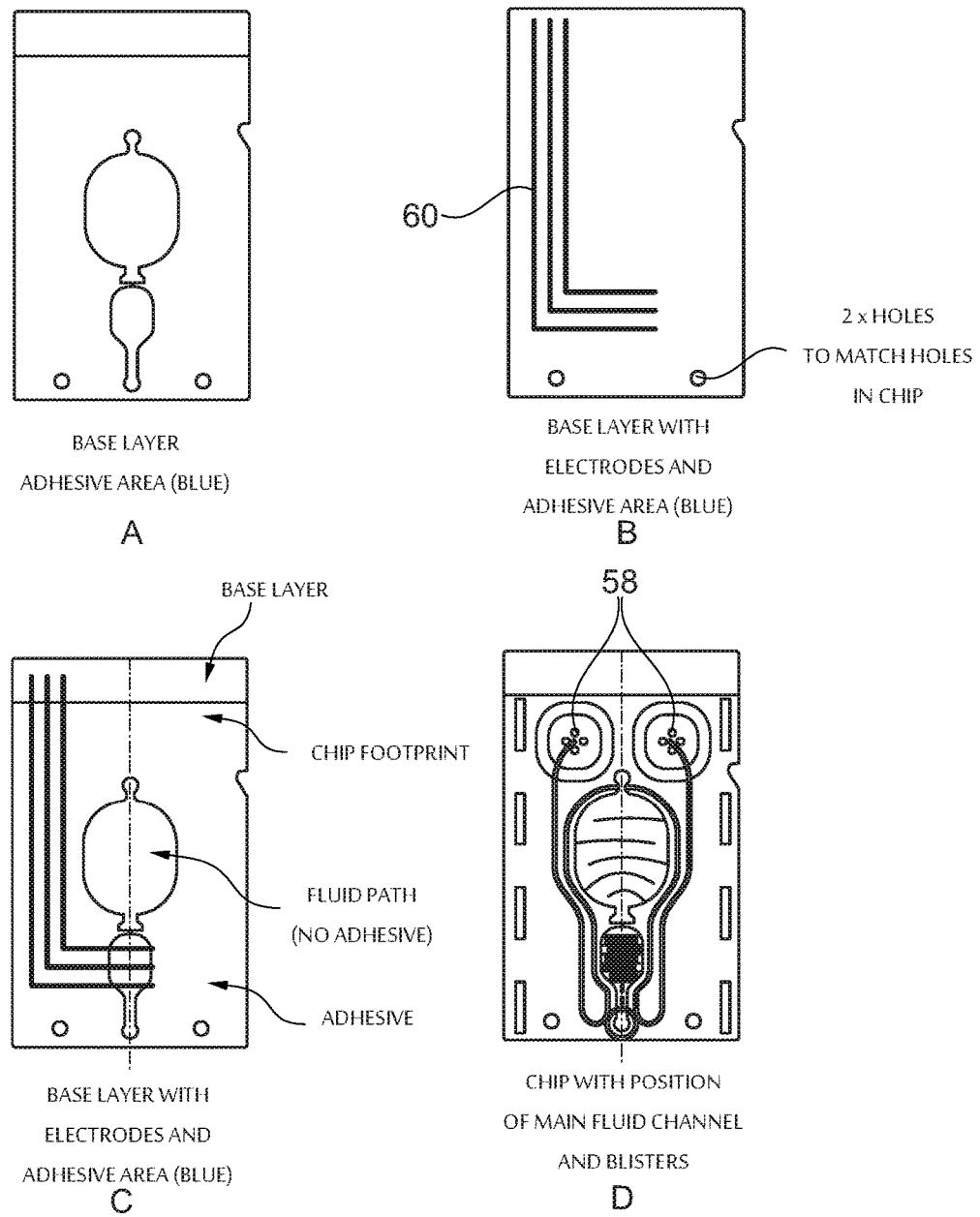
Figure 7E:
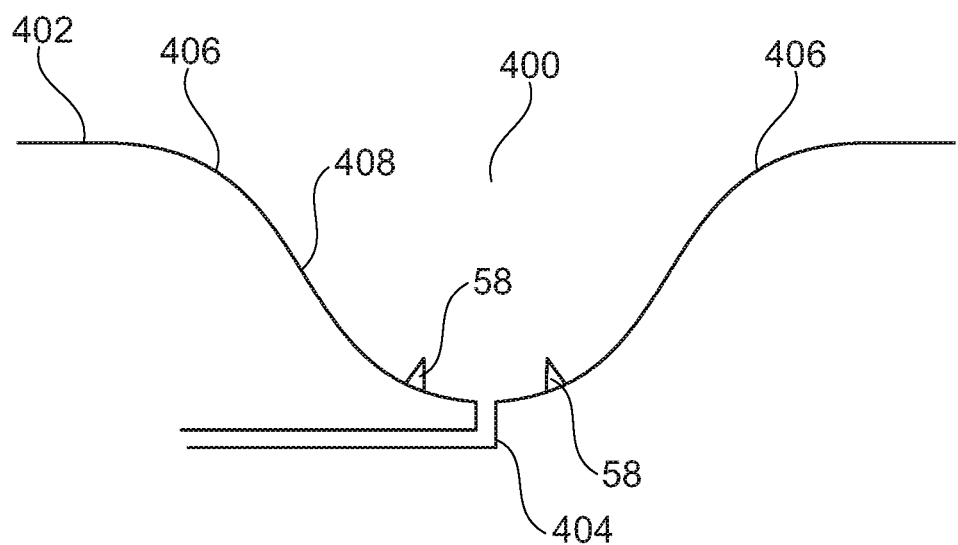
Figure 8:
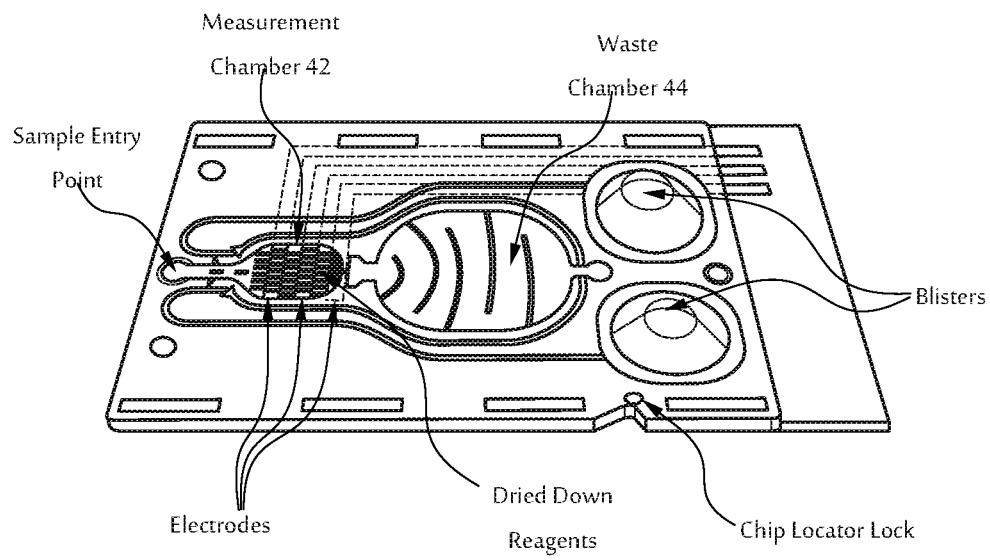
Figure 9:
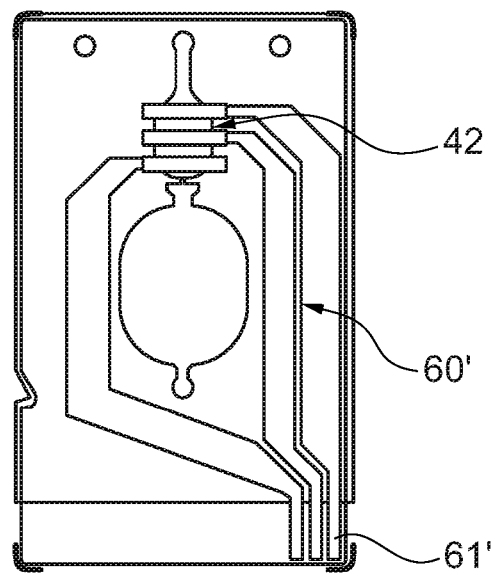
Figure 10:
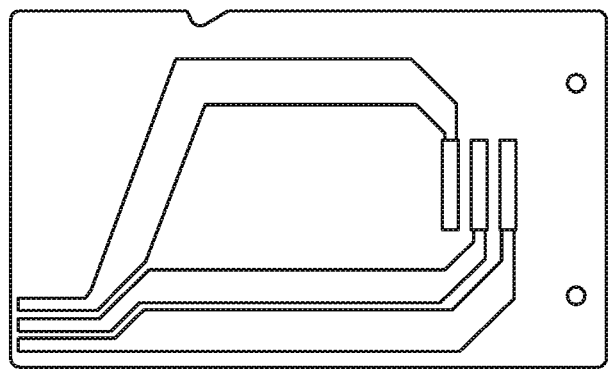
Figure 11:
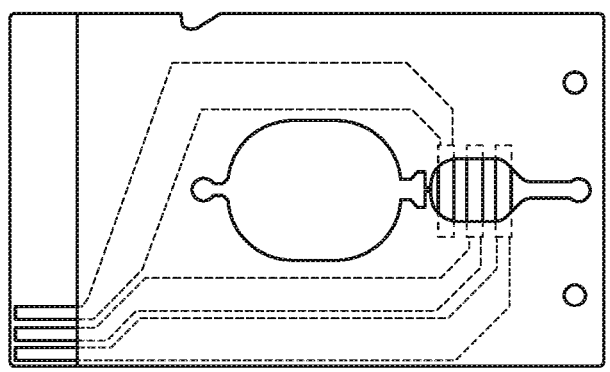
Figure 12:
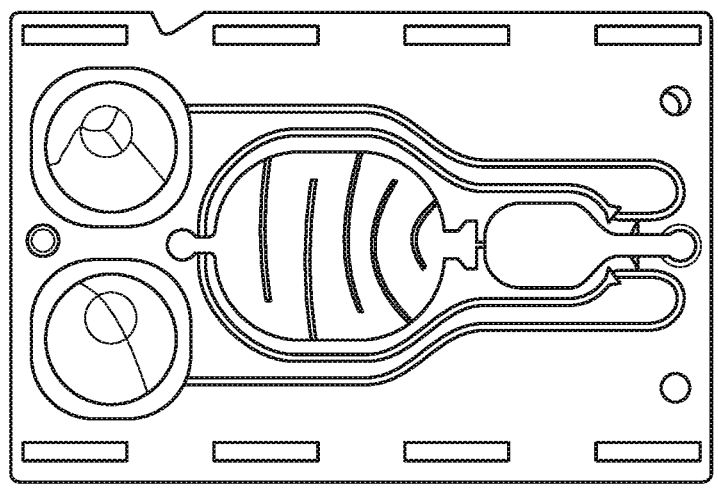
Figure 13:
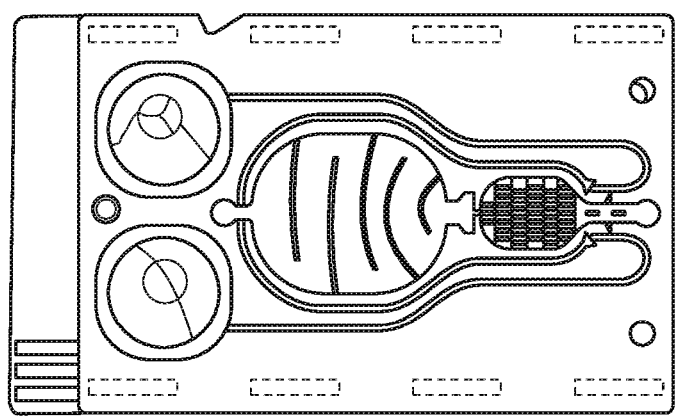
Figure 17:
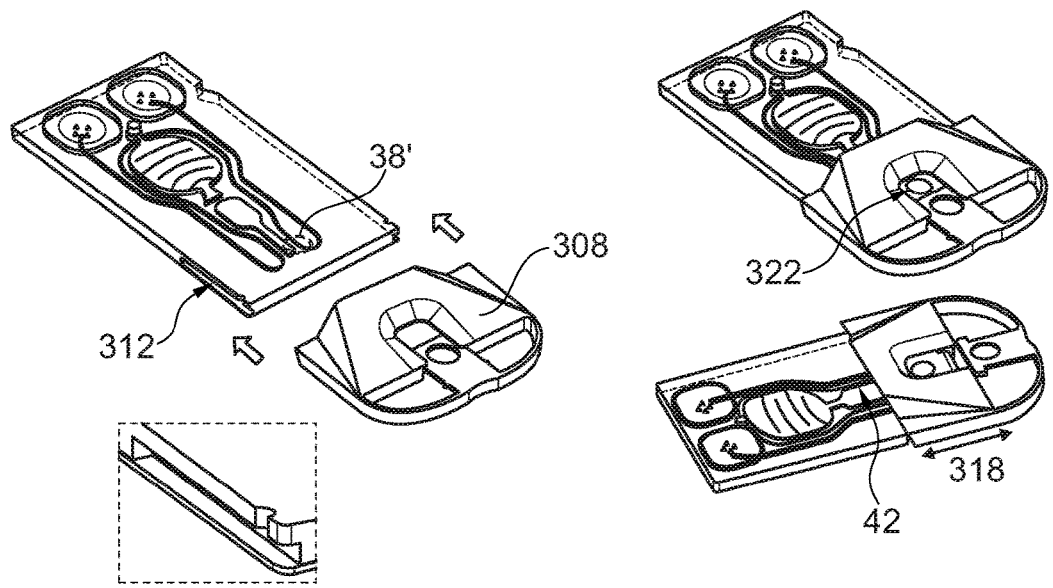
Figure 18:
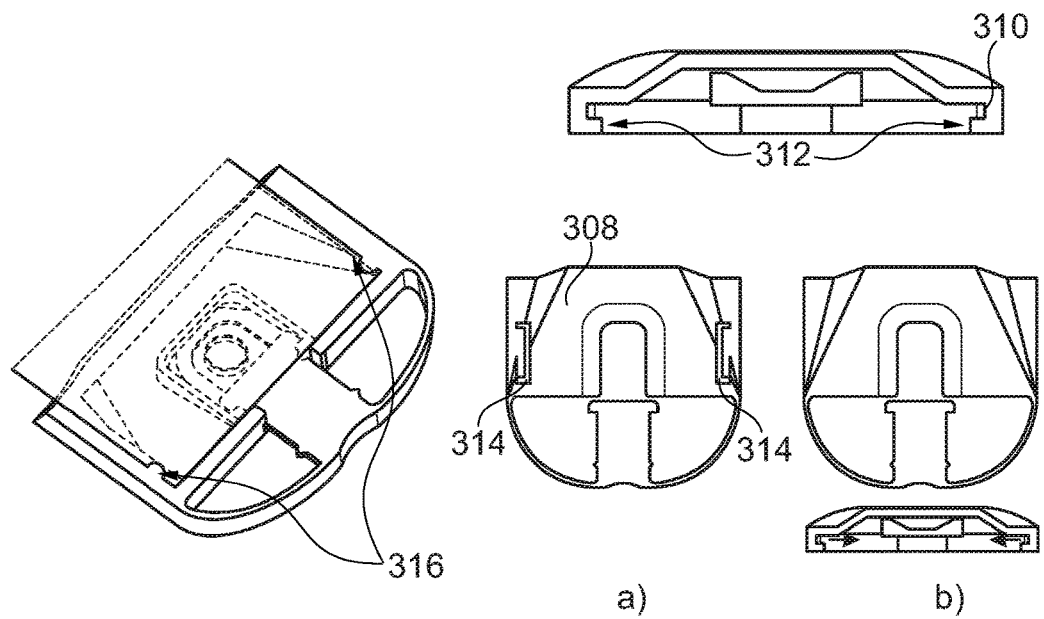
Figure 19:
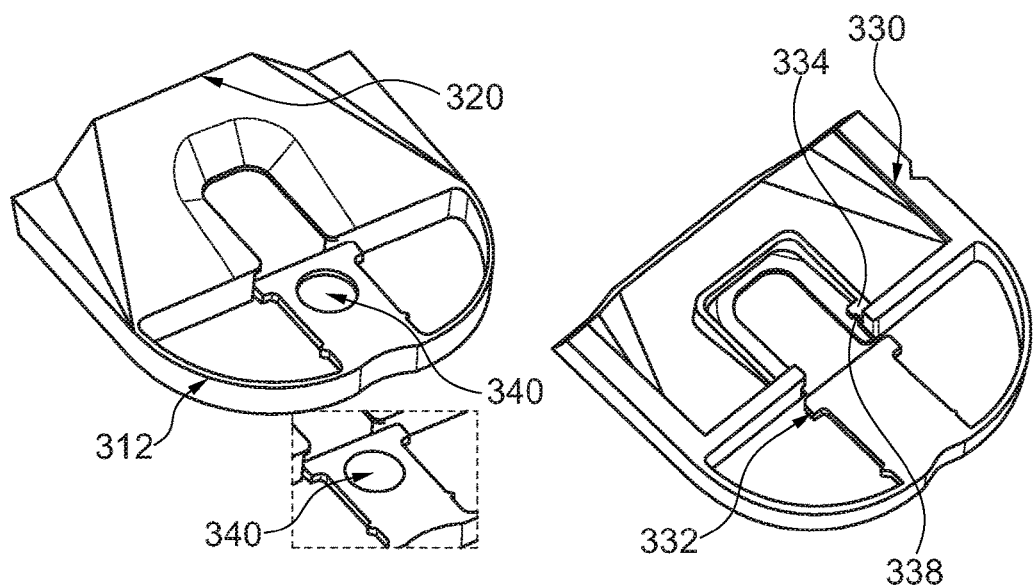
Figure 20:
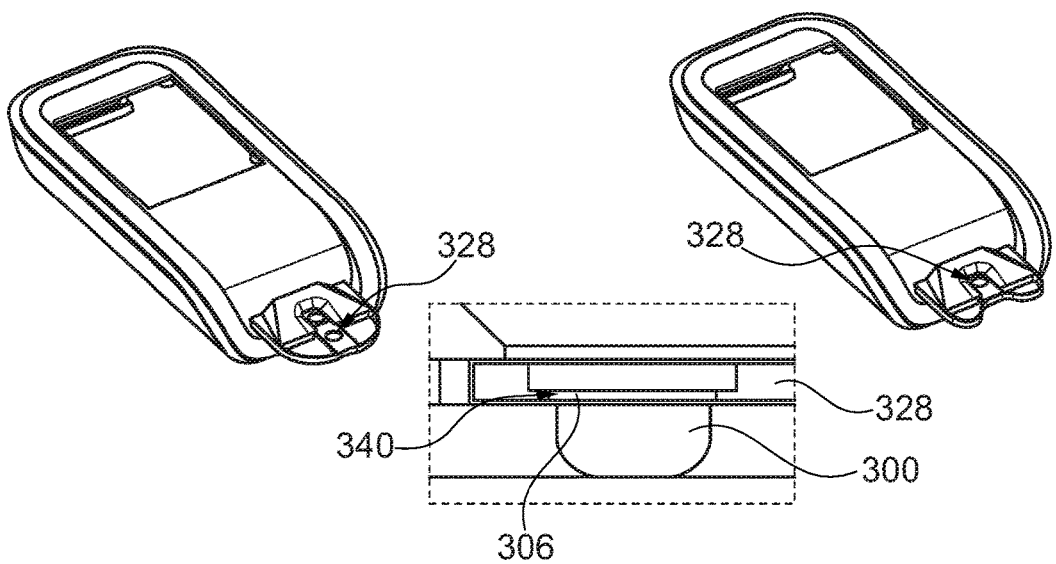
Figure 21:
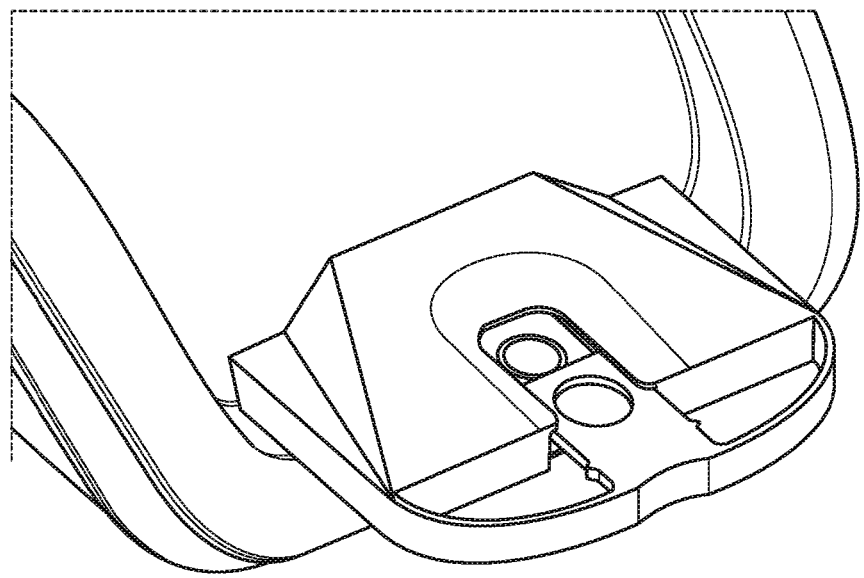
Figure 23:
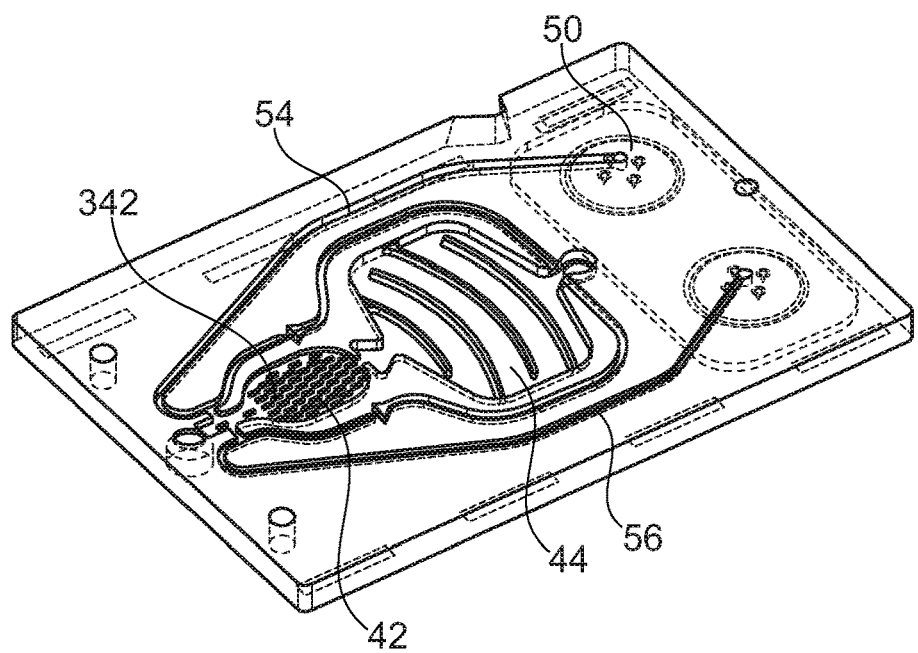
Figure 24:
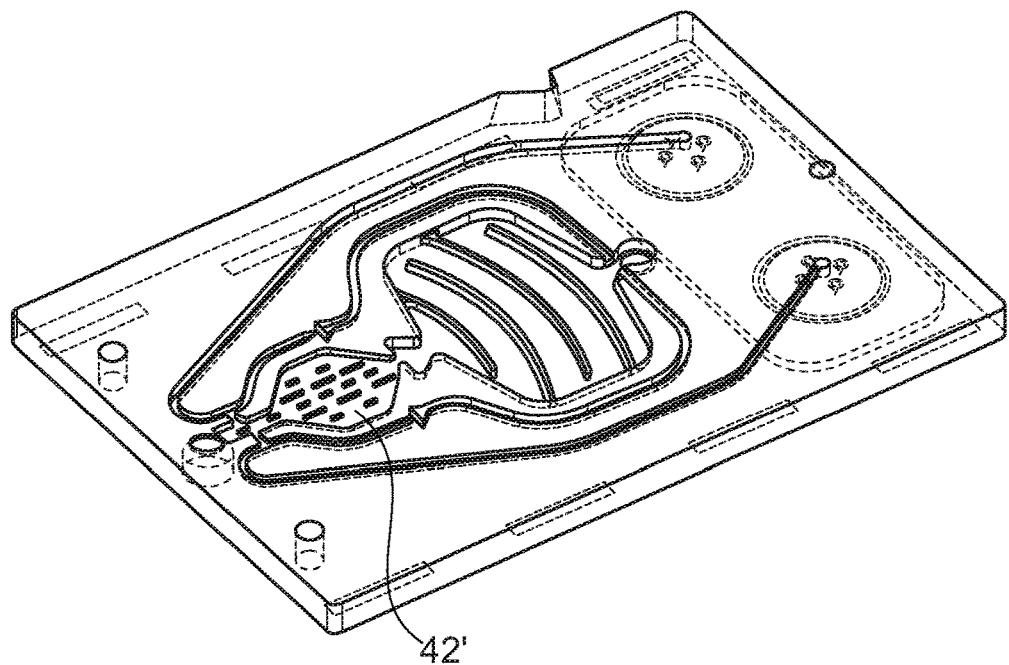
Figure 25:
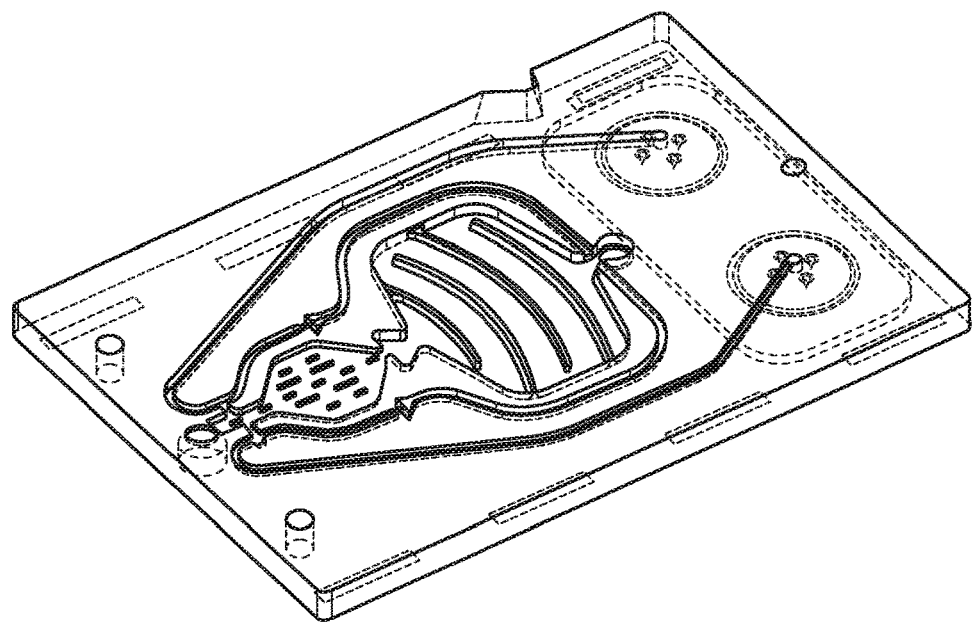
Figure 26:
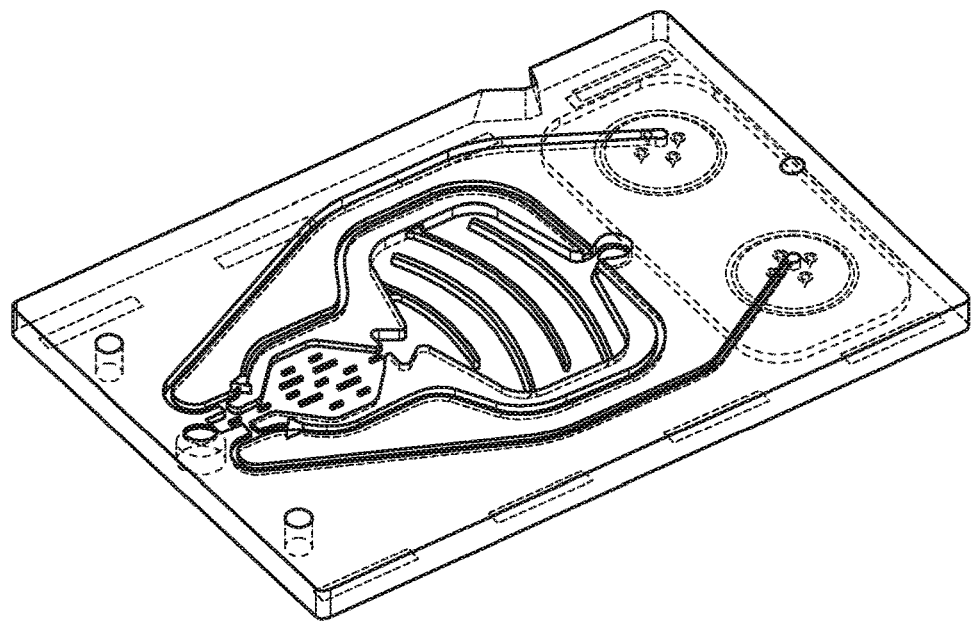
Figure 27:
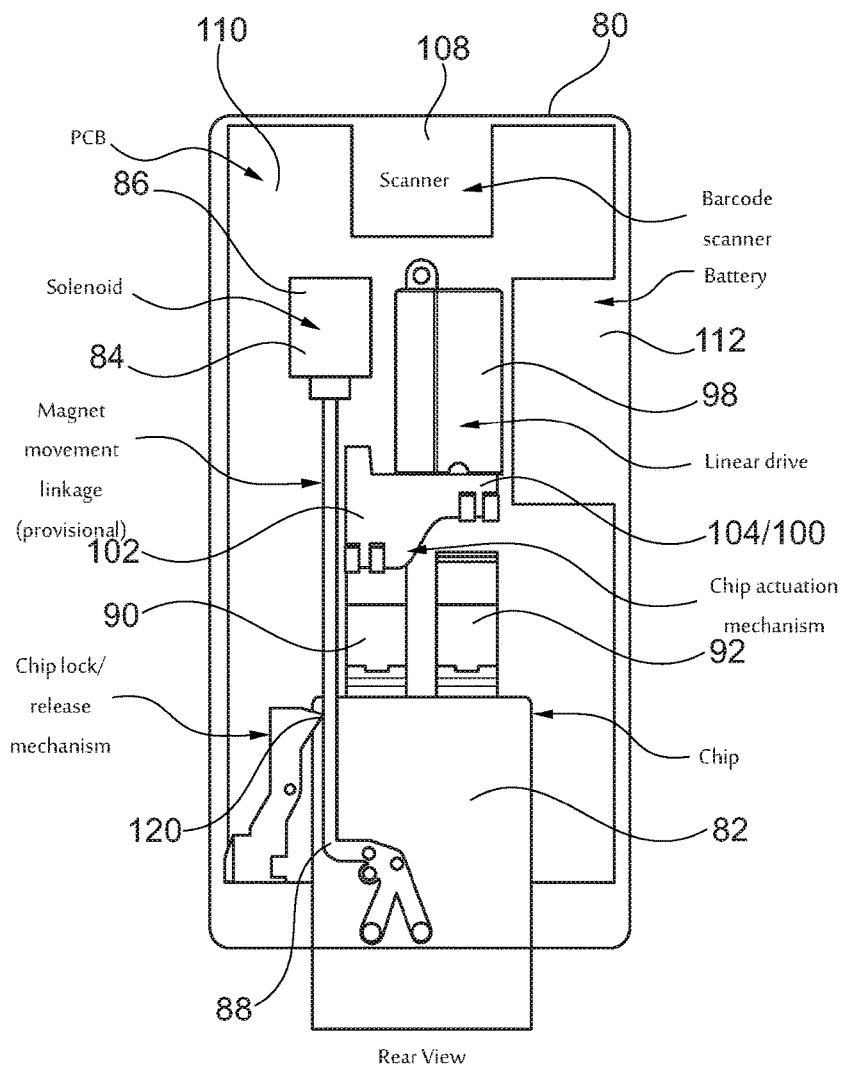
Figure 28:
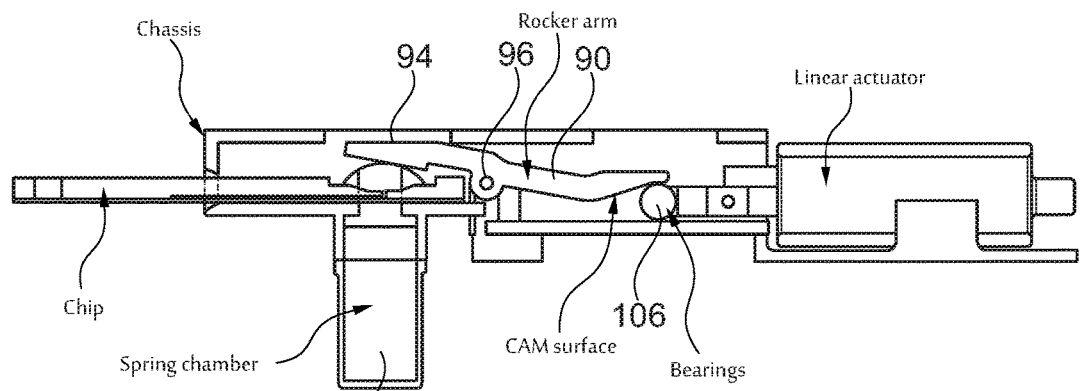
Figure 29:
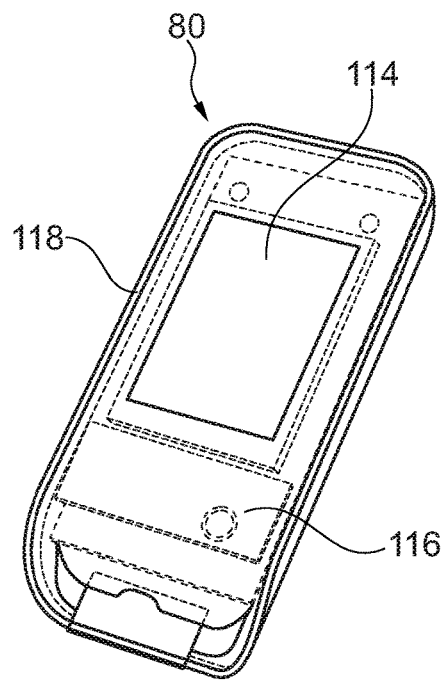
Figure 30:
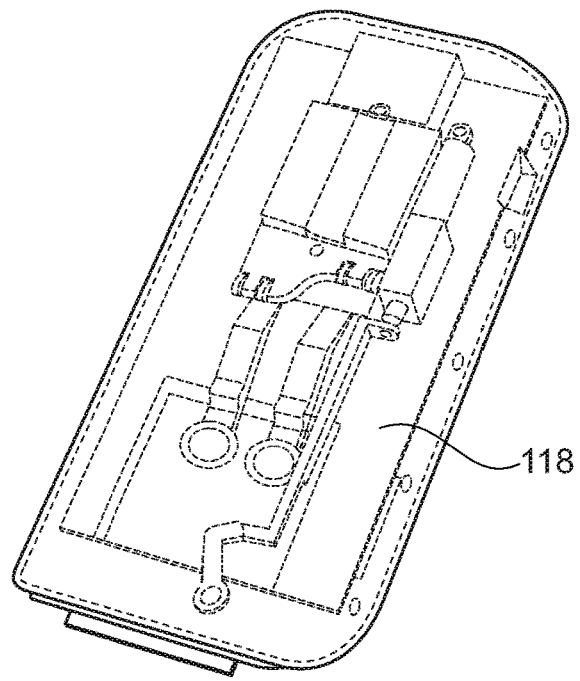
Figure 31:
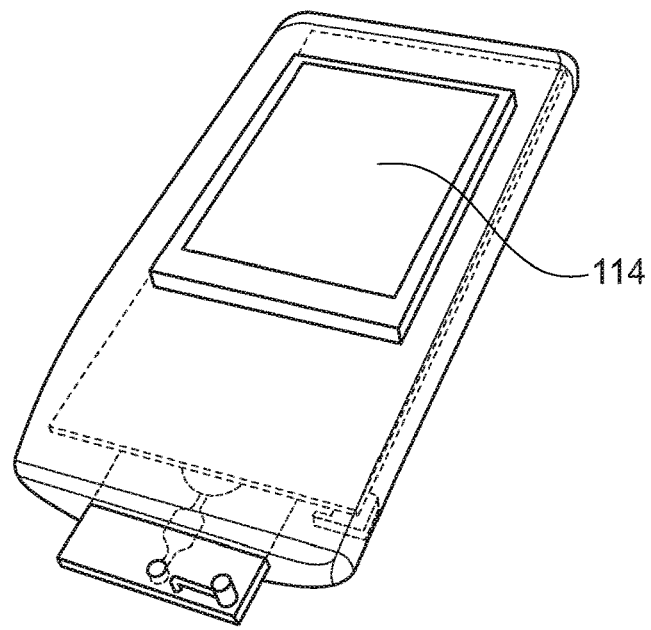
Figure 32:
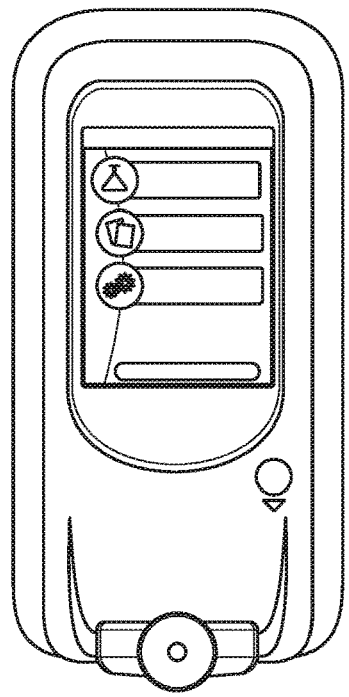
Figure 36:
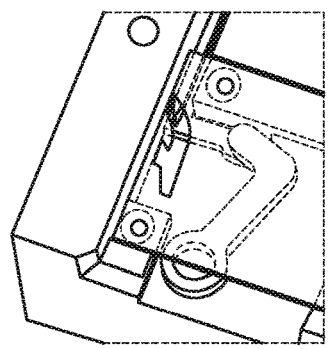
Figure 35:
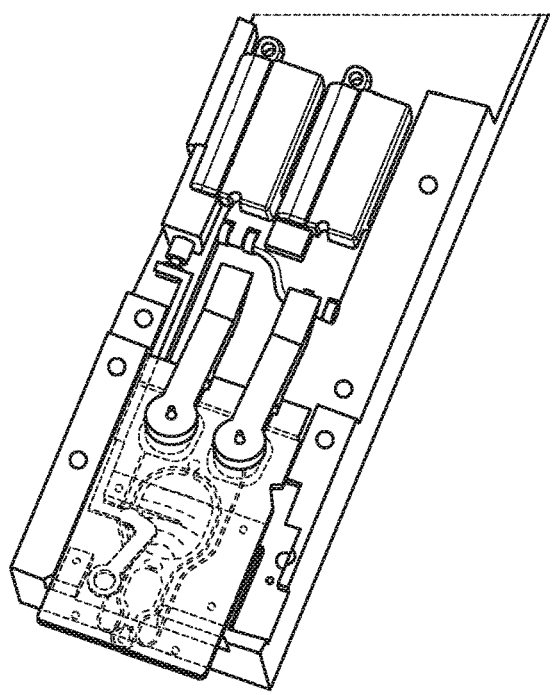
Figure 37:
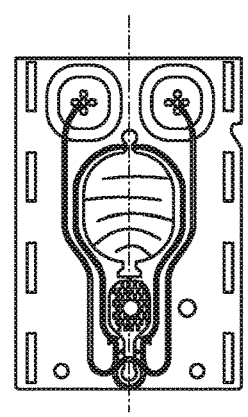
Figure 38:
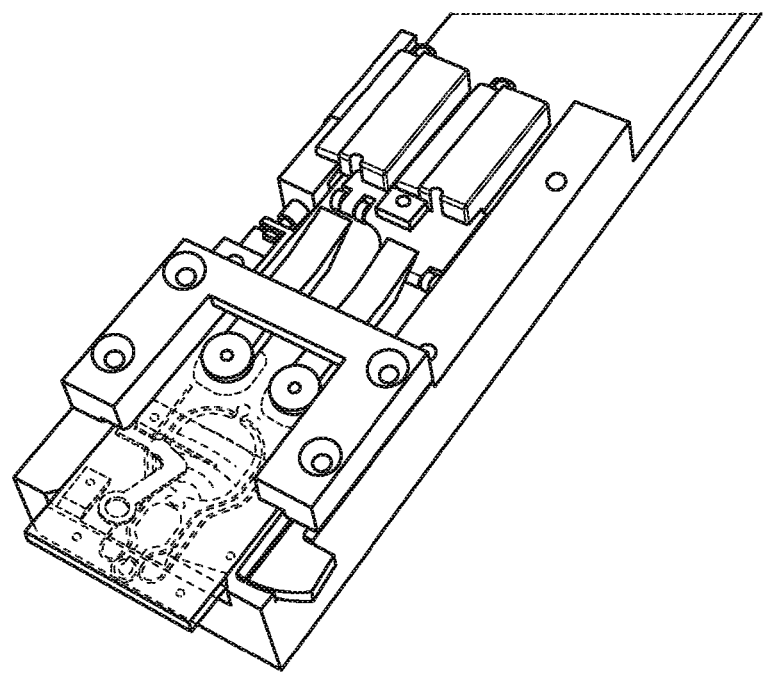
Figure 39:
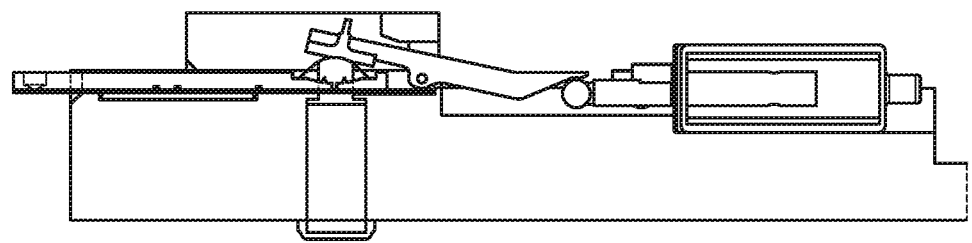
Figure 41:
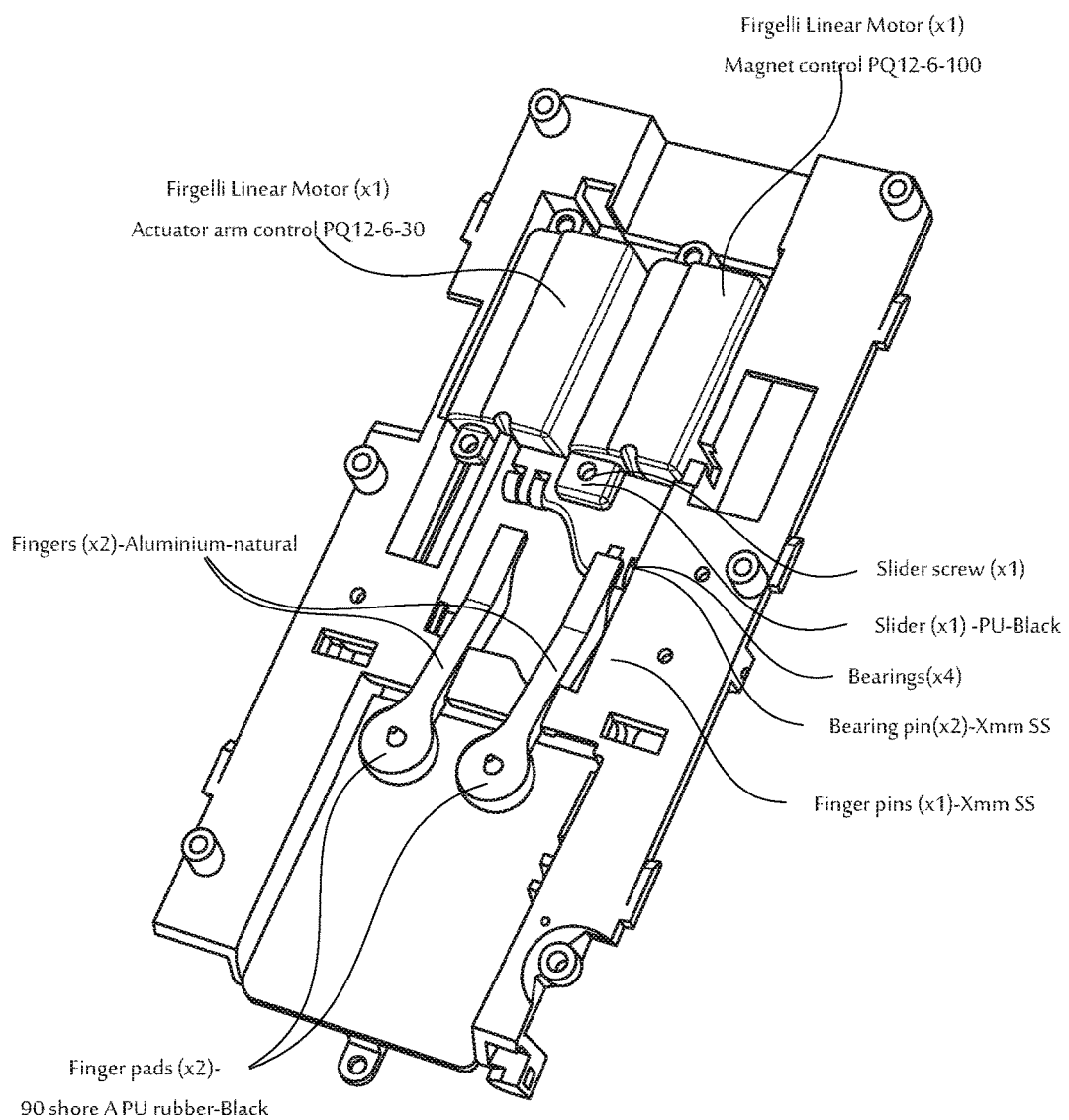
Figure 42:
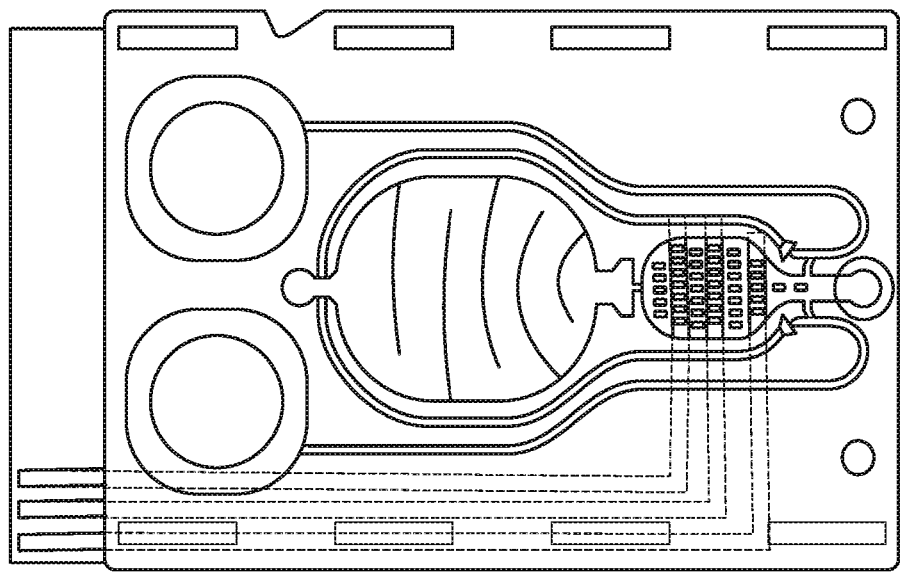
Figure 43:
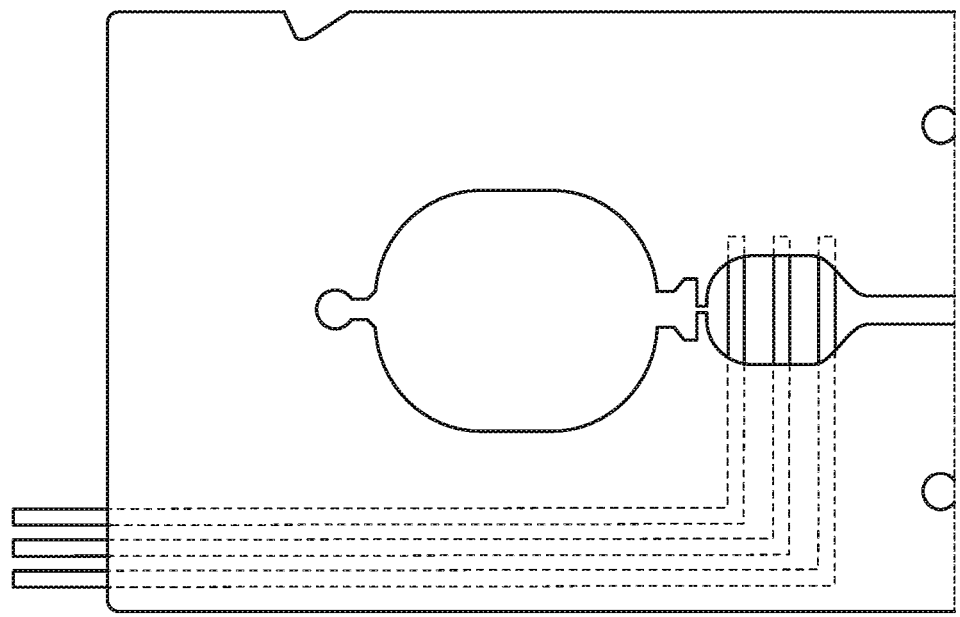
Figure 45:
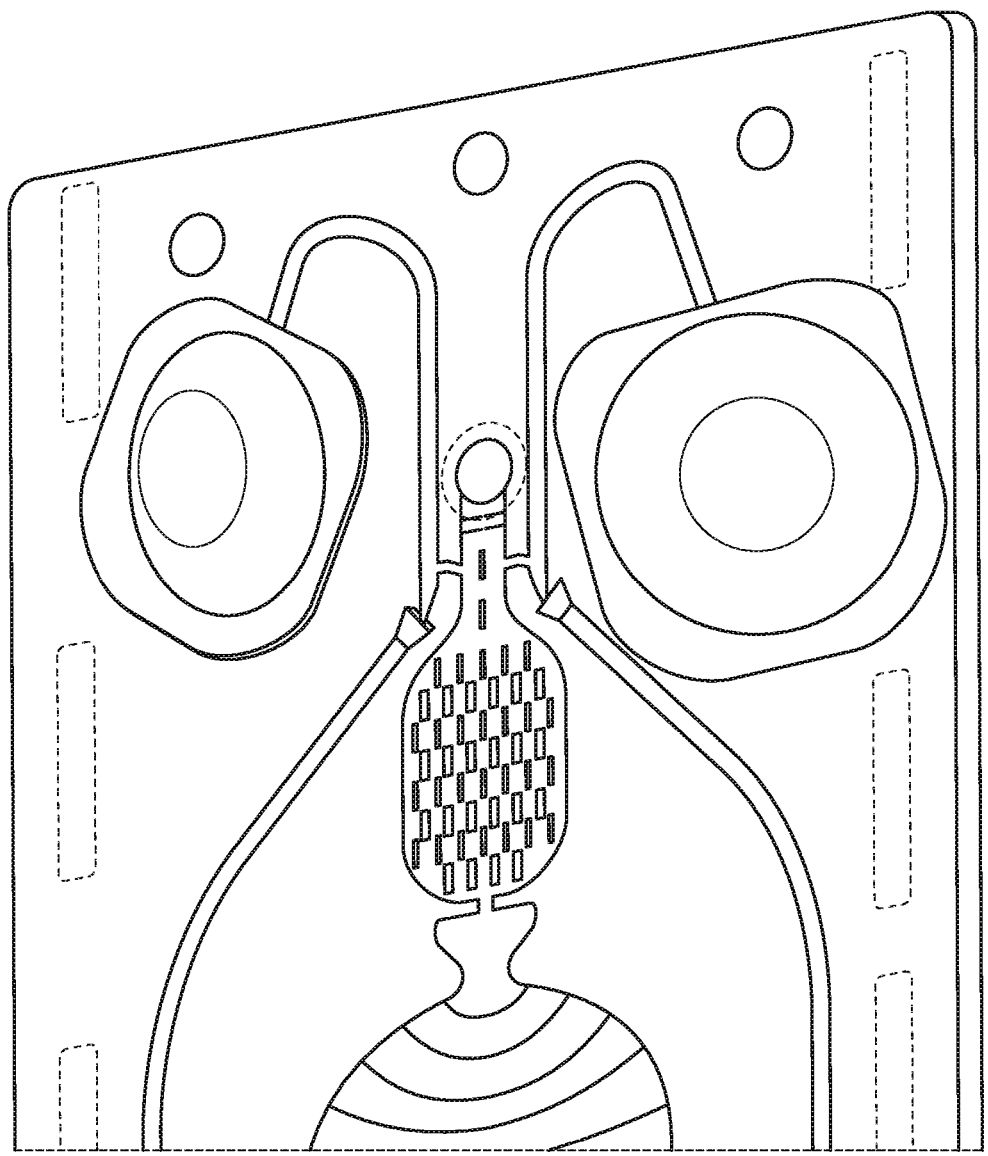
Figure 46:
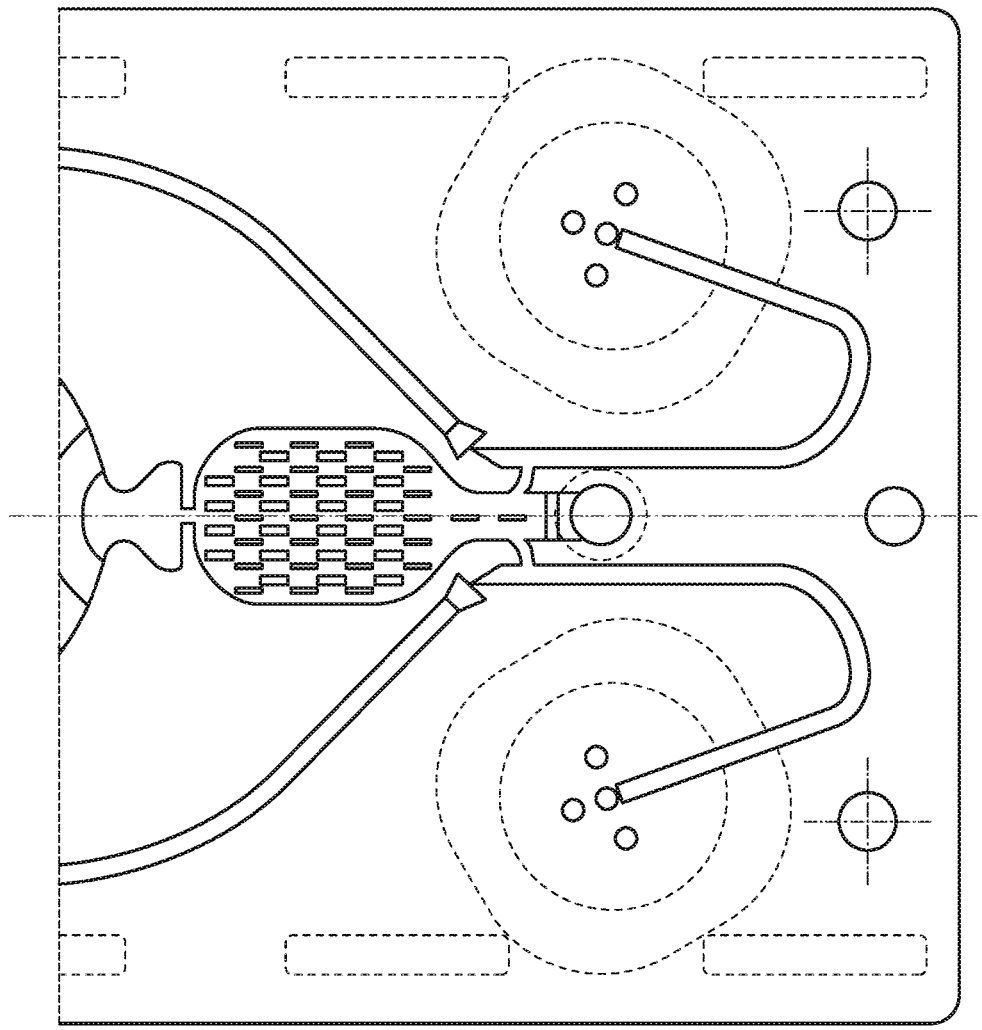
Figure 51:
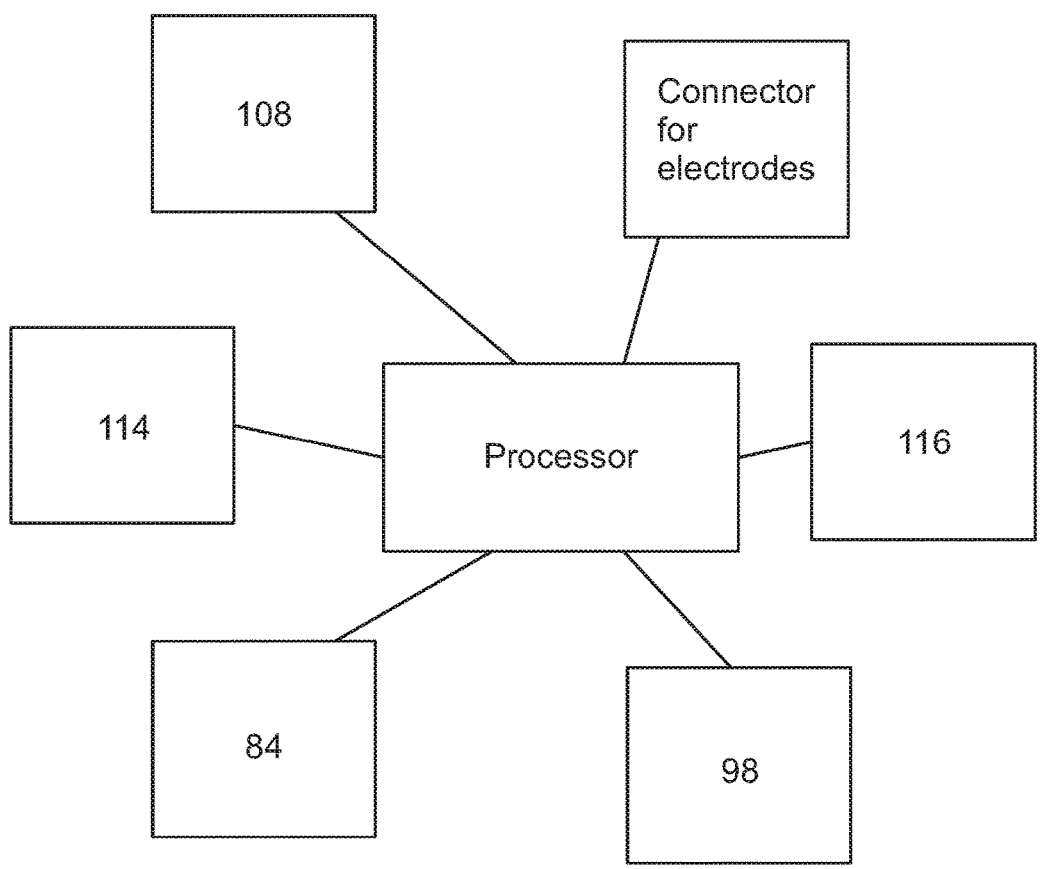
Figure 52:
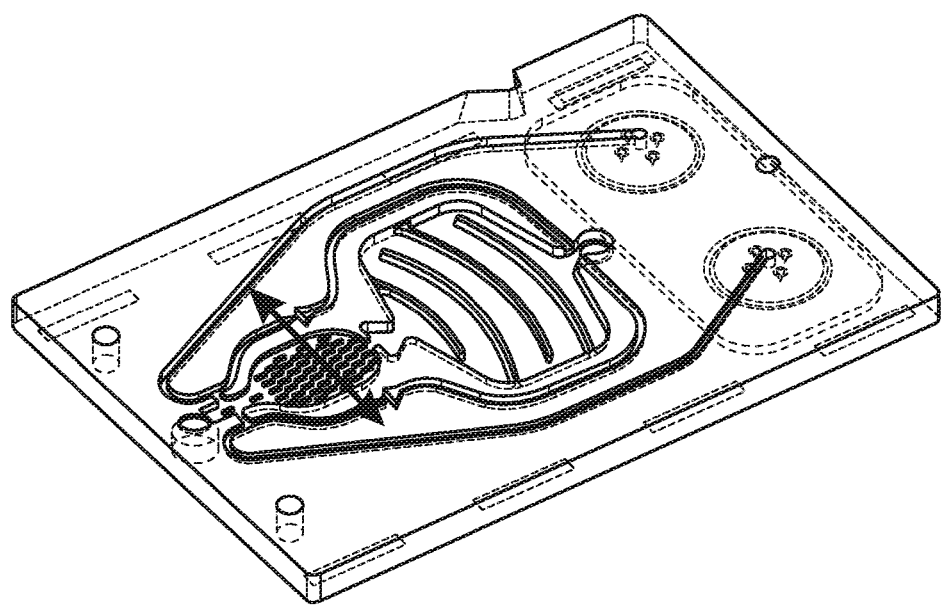

FIG. 7a-d are schematic diagrams of layers of the sample carrier of FIG. 6;

FIG. 7e is a cross-sectional schematic diagram of a recess for a blister according to the embodiment of the invention;

FIG. 8 is a further perspective view of the sample carrier of FIGS. 6 and 7;

FIG. 9 is a schematic diagram showing electrodes according to modification of the sample carrier of FIGS. 6-8;

FIG. 10 is a plan view of the electrodes depicted in FIG. 9 without dielectric;

FIG. 11 is a plan view of the electrodes of FIG. 9 with dielectric overprinted;

FIG. 12 is a plan view of a sample carrier without an electrode;

FIG. 13 is a plan view of a sample carrier including an electrode according to the modification of FIG. 9;

FIG. 14 is a schematic diagram of a sample entry point according to a modification of the sample carrier of FIGS. 6-8;

FIGS. 15 and 16 show schematic diagrams of a cover member for a sample carrier of FIGS. 6-8;

FIG. 17 shows the cover member of FIGS. 15 and 16 in various stages of being placed on a sample carrier;

FIG. 18 shows how the cover member of FIGS. 15-17 can be made so it can be slid onto a sample carrier;

FIG. 19 shows the cover member of FIGS. 15-18 as moulded;

FIG. 20 shows how a closure member is able to provide an air tight seal with the cover member of FIGS. 15-19;

FIG. 21 shows the cover member of FIGS. 15-20 on a sample carrier inserted into a test device;

FIG. 22 shows a sample carrier with a cover member according to FIGS. 15-21 in place in a test device;

FIG. 22a shows a further modification of a closure member;

FIG. 23 is a schematic diagram of a sample carrier according to the embodiment of FIGS. 6-8;

FIGS. 24-26 show schematic diagrams of modifications of the sample carrier of FIGS. 6-8 and 23;

FIG. 27 is a schematic rear cross sectional view of a test device according to an embodiment of the invention suitable for conducting an assay using a sample carrier;

FIG. 28 is a schematic side view cross section of the test device of FIG. 27;

FIG. 29 is a perspective front view of a test device of FIGS. 27-28;

FIG. 30 is a perspective rear view of the test device of FIGS. 27-29;

FIG. 31 is a perspective front view of the test device of FIGS. 27-30;

FIG. 32 is a plan view of the test device of FIGS. 27-31 showing the screen in use;

FIG. 33 is a perspective rear cut away view of the test device of FIGS. 27-32;

FIG. 34 shows components of a test device according to an embodiment of the invention;

FIG. 35 is a perspective rear cut away view of the test device of FIG. 34;

FIG. 36 is a close-up view of a magnet of the test device of FIGS. 34-35;

FIG. 37 is a plan view of the sample carrier of FIGS. 6-8;

FIG. 38 is a perspective cut away view of the test device of FIGS. 34-36;

FIG. 39 is a cross-sectional side view of the test device of FIGS. 34-36 and 38;

FIG. 40 includes several views of the sample carrier of FIGS. 6-8 and 37;

FIG. 41 is a partial cut away view of a test device according to an embodiment of the invention;

FIGS. 42 and 43 show plan views of the sample carrier of the embodiment of FIGS. 6-8;

FIGS. 44-46 show a sample carrier according to another embodiment of the invention;

FIG. 47 shows a perspective exploded view of an actuator for a test device according to an embodiment of the invention;

FIG. 48 is a rear perspective cut away view of a test device according to the embodiment of FIG. 47;

FIG. 49 is a front perspective view of a test device according to the embodiment of FIGS. 47 and 48;

FIG. 50 shows components of the test device according to the embodiment of FIGS. 47-49; and FIG. 51 shows a schematic system diagram for the test device of FIGS. 27-33; and FIG. 52 is a schematic diagram of a sample carrier according to a modification of the embodiment of FIGS. 6-8 showing movement of a permanent magnet.

It is to be understood that the Figures are provided for illustration purposes only and are not to scale. In many instances, the drawings show elements much larger that they would be in practice, as the skilled person will readily appreciate.

In this description, the term 'proximal' is used to mean nearer to a user using a test device and sample carrier when the sample carrier is in a holder of the test device. The term 'distal' is used to mean further from a user using a test device and sample carrier when the sample carrier is in a holder of the test device. A user using a test device and sample carrier is considered to be adjacent to an end of the test device that contains an opening for inserting the sample carrier into the holder.

FIGS. 1 to 5 and the accompanying description below provide an example of a chemical analysis method suitable for being performed in the apparatus devices disclosed herein. Further details of this chemical assay are disclosed in WO2009/068862, which is incorporated herein by reference. In addition, sample carriers and test devices for performing chemical assays are disclosed in WO2010/004244 and WO2010/004241, both of which are incorporated herein by reference.

The illustrated chemical analysis steps are just one of a variety of examples for which the apparatus disclosed herein could be configured to work.

Figure 2:
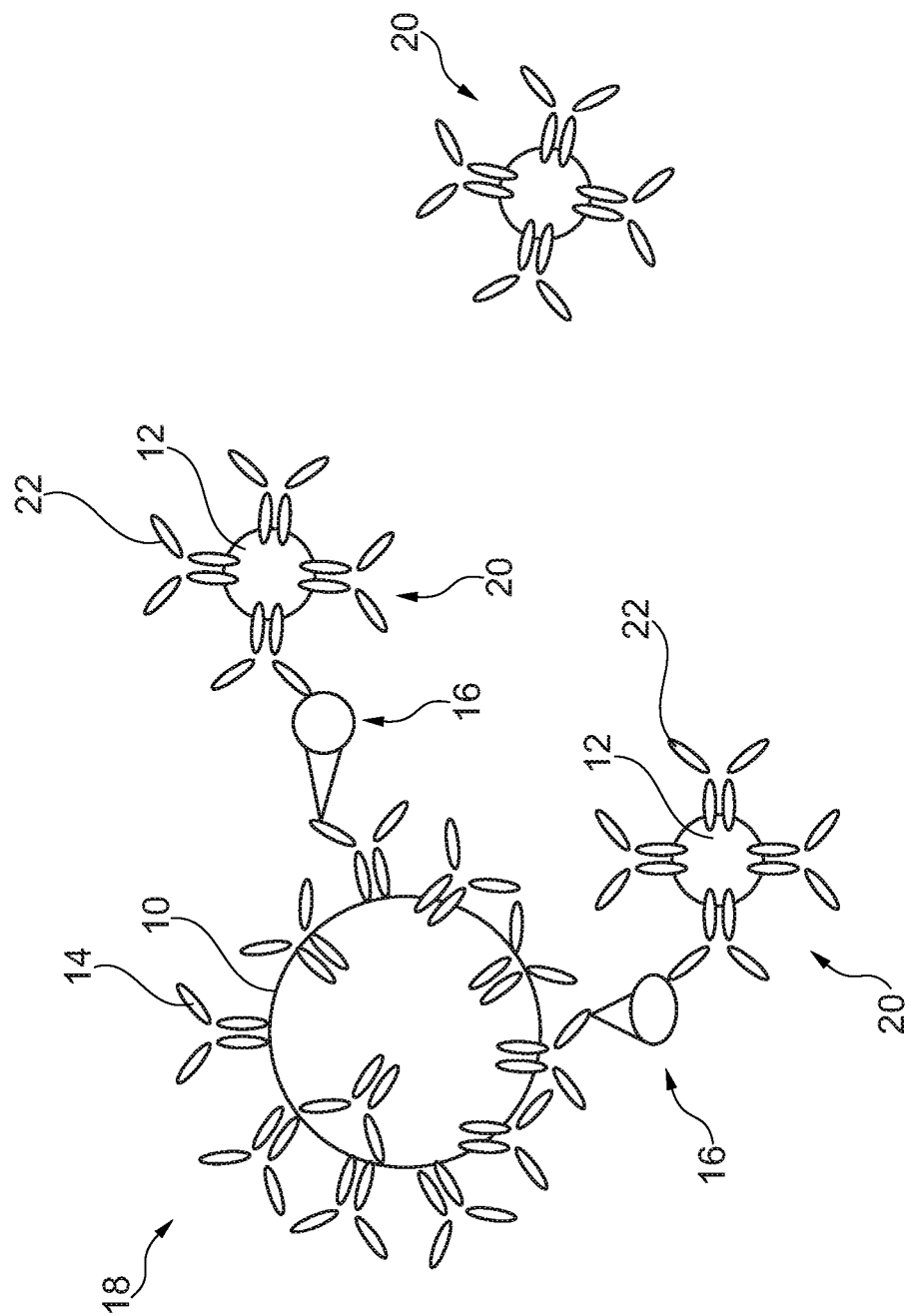
FIG. 2 is a schematic diagram showing the elements of FIG. 1 bound together in a first stage of the analysis procedure.

As shown in FIGS. 1 and 2, the method shown utilises a carrier element, in this case magnetic particle 10, preferably a super paramagnetic particle such as an arsenic solid phase, and a label element, in this case metal label, typically a particulate label which is preferably a silver sol 12. Silver is preferable as it forms stable sols which can easily be oxidised to form silver ions. The magnetic particle 10 is attached to a first binding moiety, preferably one or more antibodies 14, which is capable of binding to an analyte of interest. The analyte of interest is preferably an antigen 16 but can also be an antibody, a mimotype or nucleic acid strand. The magnetic particle 10 with its attached antibodies 14 forms a magnetic support 18.

The silver sol particle 12 is attached to a second binding moiety to form a metal label 20. The second binding moiety, preferably one or more antibodies 22, is capable of binding to a different region of the antigen 16.

In practice, a plurality of magnetic particles 10 and labels 12 is provided in dried form or in solution or suspension, for reaction with a plurality of antigens 16 in a sample to be tested.

Referring next to FIG. 2, the elements of FIG. 1 are shown once they have become bound to one another, typically after an incubation period in a suitable reaction chamber, examples of which are described below. An antibody 14 of the magnetic particle 10 and an antibody 22 of the particulate label 12 bind to an antigen 16, in effect sandwiching the antigen 16 between them. A plurality of antigens 16 can be bound to each magnetic particle 10. The composition is such that only the right antigen 16, that is the antigen sought to be detected and measured, can bind to the antibodies 14 and 22 of the magnetic particle 10 and label 12. Any other antigens or other substances in the mix will not bind to the magnetic particle 10 and neither to the label 12.

The combination is such that the antigens 16 become attached to a carrier element, the magnetic particle, as well as to a label element, in this example the silver sol particle 12. The antigens can thus be isolated from the remainder of the sample and then to be detected, in particular by using the silver of the label 12, as described below.

Referring now to FIGS. 3 to 5, these depict in graphical form the binding of the various elements together, the separation of the magnetic particles from the remainder of the solution or suspension and the detection of the labels carried by the antigens. For ease of description, the three stages shown are depicted as the incubation stage, the separation stage and the detection stage. The term incubation is not intended to imply any particular process apart from allowing the sample to mix with the carrier and label particles and to allow the element to be tested to be attached to these.

FIG. 3 depicts the incubation stage, in which in a suitable mixing chamber and in some examples held in a suitable inert carrier fluid there are provided a plurality of magnetic particles 10, a plurality of labels 12 and then a specimen to be tested. In this example, the specimen includes a plurality of antigen particles 16. The antigen particle 16 is depicted as being of a particular type, shown as a particular shape in the drawing. The antibodies 14 and 22 of the particles 10 and 12 respectively are compatible only with that antigen 16 and are depicted as having complementary shapes. In this schematic representation, the magnetic particle 10 is shown having a single antibody particle 14 but in practice will be provided with a plurality of these.

Thus during this first phase the antigen 16 binds to the antibodies 14 and 22 to form the complex shown at the right hand side of the Figure. Any other antigens in the specimen will not bind either to the magnetic particle 10 or the label 12 and thus will remain isolated in suspension. These antigens could be said, following the representation in FIG. 3, to have a different shape with which the antibodies 14 and 22 are not compatible.

FIG. 4 shows the second phase in the procedure, that is the separation phase. The magnetic properties of the particles 10 are used to hold these in position while other particles are washed to a second, waste chamber. Typically, this is achieved by the generation of a magnetic or electromagnetic force used to hold the magnetic particles 10 in place while other particles, in particular labels 12 which have not become bound to a magnetic particle 10, are washed away with a wash solution. Apparatus and methods for achieving this are described in detail below.

During separation, therefore, all or substantially all of the labels 12 which are not bound to a magnetic particle 10 are removed from the chamber as well as any antigens 24 incompatible with the antibodies 14, 22, that is antigens not desired to be analysed. What is left in the chamber are magnetic particles 10, some of which may be bound to labels 12.

Referring now to FIG. 5, there is shown the final phase of the process, that is the detection phase. After the chamber has been washed with the wash solution, a detection solution can be provided to the chamber and the silver sol is oxidised. This in effect dissolves the silver of the label and produces silver ions which dissolve into the carrier fluid. It will be appreciated that since only the correct antigens 16 will have been held in the chamber while it was washed and since only these will carry with them a label 12, the amount of silver ions produced by oxidation will be directly related to the number/amount of the antigens sought to be detected in the original specimen. Any magnetic particles 10 which do not carry any antigen 16 will not carry a label 12 either and thus will not affect amount of silver ion generated by oxidation.

In one embodiment, the detection solution includes ammonium thiocyanate which removes the silver sol from its biocomplex and forms a monolayer chemically bound around the silver sol resulting in a negatively charged nanoparticle. This charged nanoparticle can be migrated under an electrical potential to a positively charged electrode. The silver sol at that electrode is then dissolved under an oxidative potential to form silver ions Ag+, which can then be measured by accumulation stripping voltammetry (ASV). ASV is an analytical technique that involves pre-concentration of a metal phase onto an electrode surface and selective oxidization of each metal phase species during an anodic potential sweep.

A small proportion of the silver ions measured may be in the form of a complex with a chelating agent where the release agent is capable of chelating the silver ions.

The use of silver sol as a label 12 gives a molecular amplification of the electrochemical signal, as each 40 nm silver sol particle contains approximately 106 silver ions. Thus the sensitivity of the assay is enhanced and only a small amount of sample is required. Furthermore, silver forms stable sols for use as a biolabel. It also easily oxidized to form silver ions.

FIGS. 1 to 5 and the above description relate to just one example of a suitable collection and detection procedure using a particular antibody/antigen mechanism, and labelling arrangement and oxidation method. However, the apparatus and methods described below are not limited to the application of this method alone and could be used with other detection mechanisms, that is with different analyte capturing and detecting mechanisms, as well as with other label detection methods.

As shown particularly in FIG. 6, a sample carrier 30 according to a preferred embodiment of the invention includes a substrate 32. The sample carrier 30 includes a proximal end 34 and a distal end 36. At the proximal end 34 is provided a sample entry point 38 which is coupled by a channel 40 to a detection or measurement chamber 42. The detection or measurement chamber 42 is distal of the sample entry point 38. The detection chamber 42 is preloaded with reagents in a dried form. In some embodiments of the invention, the dried down reagents are dried carrier elements and label elements with appropriate binding moieties such as described above. The detection chamber 42 is coupled to a waste chamber 44 via a valve 46. The valve is configured to allow fluid flow under pressure from the detection chamber 42 into the waste chamber 44 but not vice versa. The waste chamber can include barriers 48 providing a tortuous pathway to minimise flow of fluid from the waste chamber 44 to the detection chamber 42. The waste chamber 44 is distal of the detection chamber 42. The waste chamber 44 can include a vent to allow egress of air from the waste chamber 44 as other fluid enters via the valve 46.

Distal of the waste chamber 44 are provided a first storage chamber 50 and a second storage chamber 52. The first and second storage chambers 50, 52 are coupled to the channel 40 respectively via channels 54 and 56. In this embodiment, the first and second storage chambers 50, 52 are foil filled blisters beneath which are provided pins 58 for bursting the blisters when the blisters are compressed. The number of pins 58 is not important. However, in this embodiment there are four beneath each of the blisters 50, 52, as shown more clearly in FIG. 7d.

FIG. 7e shows a recess 400 into which a blister can be compressed and burst. The recess 400 is a recess of a surface 402 of the sample carrier. Within the recess are provided pins 58, two of which are not visible in FIG. 7e. At an apex of the blister is coupled a conduit 404 through which fluid from the blister can exit the recess 400. The recess 400 has a curved shoulder 406 around a perimeter of the recess 400 where the recess 400 meets the surface 402. The curved shoulder has a gradually increasing incline from the surface 402 to a point of maximum gradient 408 whereafter the incline gradually reduces to the apex of the recess 400. An advantage of this arrangement is that as a blister is pushed into the recess 400, the curved shoulder 406 causes an underside of the blister to flex causing the blister to flex evenly and fully into the recess. When the blister is pressed upon the pins 58, the blister is burst and fluid exits the blister via the conduit 404. Because the blister has flexed evenly and fully into the recess, minimal fluid is left behind in the blister as there are no sharp corners to trap fluid. In addition, the flexing of the blister forces air out of the recess, minimising air in the system which, for the reasons explained elsewhere, can cause erroneous readings.

In embodiment of FIG. 6, the first storage chamber 50 is preloaded with a wash solution, and the second storage chamber 52 is preloaded with a detection solution. However, for tests other than the one described above, the first and second storage chambers 50, 52 may be preloaded with other fluids, preferably liquids or solutions. In addition, depending on the test required there can be more or fewer than two storage chambers coupled to the detection chamber. However, preferably all storage chambers are distal of the detection chamber.

Extending from the distal end 36 of the sample carrier 30 to the detection chamber 42 are detection terminals, in this embodiment electrodes 60, for detecting a characteristic of a sample in the detection chamber. The number of electrodes will depend on the requirements of the test to be performed. In the depicted embodiment, there are three electrodes each in the form of a sensing section in the detection chamber and a carbon electrically conductive track on the sample carrier. The electrodes are printed on a non-reactive surface so as not to interfere with biological or other reactions nor materials used for the test or the resistance or signal from the assay. At the distal end 36 of the sample carrier 30 is provided a connector 61 for electrically connecting the tracks to a test device as described below. In other embodiments, the detection terminals can be types other than electrodes. For example, the detection terminals can be optical terminals, resonance terminals, plasmatic terminals, vibrational (such as Raman) terminals or acoustic wave terminals. They can be designed for fluorescence, chemiluminescence, or enzyme-linked, colourimetric immunoassay for example. The sensing section and conductive tracks of the electrodes in this embodiment are both carbon ink. However, they can be different materials. For example, either or both can be gold, copper or platinum, selected on the basis of the test to be performed and/or the reagents.

The sample carrier 30 is also provided with a detent 62 which can be used for holding the sample carrier in place within a test device.

The sample carrier 30 can also be provided with an identifying code such as a barcode identifying the type of tests for which it is suitable.

The sample carrier 30 can be operated as follows. The following description of operation relates to the depicted embodiment in which the sample carrier is for performing an assay using magnetic carrier elements and label elements such as described in respect of FIGS. 1-5. However, the skilled person will be able to adapt this for other types of test.

First, the barcode is scanned by a scanner provided on a suitable test device. Examples of suitable test devices are described below.

Once a user has determined that the sample carrier is for the appropriate test, the sample carrier 30 is inserted into a holder of the test device distal end first. As the sample carrier 30 is inserted into the holder of the test device, the test device does not compress either of the chambers 50, 52.

The sample carrier 30 is inserted into the holder until the detent 62 interlocks with a corresponding element on the test device to hold the test device in position.

The user then applies the sample to be tested to the sample entry point 38 and then seals the sample entry point. Once he/she has done this, the user indicates to the test device or the test device senses that the sample has been inserted. The test device will then wait for a predetermined delay to allow for incubation of the sample. During this predetermined delay, the sample to be tested will be drawn through the channel 40 by capillary action into the detection chamber 42 where it will mix with and bind to carrier elements and label elements such as described above. Mixing can be enhanced by a test device operating a magnet arrangement such as described below to cause movement across the detection chamber of magnetic particles within the suspension thereby improving mixing and thus improving sensitivity by increasing the opportunity for binding events to occur.

After the predetermined delay, the test device will apply an electromagnetic field/magnetic field to the detection chamber 42 over the central of the three electrodes in order to hold magnetic carrier elements in the detection chamber in position. The test device will then compress the first storage chamber 50, bursting the blister and causing wash solution to be forced through channel 54 and into channel 40 and thereby into the detection chamber 42. The pressure of the wash solution will force particles which are not held in position by being bound to a magnetic carrier element through the valve 46 into the waste chamber 44.

After a predetermined period sufficient to allow washing of the detection chamber 42, the test device will compress the second storage chamber 52, bursting the blister and forcing detection solution through channel 56 and into channel 40 thereby into the detection chamber 42.

The second storage chamber 52 is a smaller volume than the first storage chamber 50 so that the compression of the second storage chamber 52 does not cause the detection solution to wash through the valve 46 into the waste chamber 48. In one embodiment the first storage chamber 50 can be 3 mm high and hold 180 ml and the second storage chamber can be 2.4 mm high and hold 100 ml.

As described above, the detection solution will react with the bound label and carrier elements in the detection chamber and allow the label elements to be read by the test device using the electrodes 60.

Once the assay is complete, the sample carrier can be disposed of.

A modification of the above described sample carrier is shown in FIGS. 9-13. In the above described embodiment, the tracks of the electrodes 60 are substantially parallel and of substantially equal width. However, this configuration can result in erroneous readings when making measurements during an electrochemical assay.

It has been discovered that a problem with the configuration is that the resistances of the tracks are different, and this can cause erroneous readings.

As per the above embodiment, in the modification of FIGS. 9-13, electrodes 60' include electrically conductive tracks on the sample carrier. However, in the modifications of FIGS. 9-13, the tracks are configured so that they each provide an equal electrical resistance between the sensing sections of the electrode in the detection chamber and the connector 61' at the distal end of the sample carrier.

As can be seen from FIGS. 9-13, how this is done is to vary the path and the width of the tracks in order to provide a desired resistance to each of the tracks. For example, a longer path length will increase the resistance of the track, whereas a greater width will reduce the resistance of the track. Accordingly, the tracks are configured so that an order of the tracks by path length is the same as an order of the tracks by width. In other words, if a track has a longer path length than another track, it will have a greater width in comparison to that other track. Preferably, the path length of a track is related to a width of that track in accordance with a predetermined relationship. The width of a track can refer to an average width of the track.

In a further modification, as shown in FIG. 14, the sample entry point 38' includes a bowl 300 for receiving a sample from a user. The bowl 300 is configured to have a volume corresponding to the volume of sample which will provide an effective test in the sample carrier. It is important that the sample carrier receives the correct amount of sample, since too little will leave air in the sample carrier which may have an adverse effect on readings, and too much may result in excess sample leaking out of the sample carrier, with consequential hazardous results. Preferably, the volume of the bowl corresponds to a combined volume of the detection chamber and the channel 40 since this is the amount of sample which will fill the sample carrier sufficiently for an effective test.

The modification of FIG. 14 also includes a closure member described below which is able to close and seal the bowl 300 in order to prevent the sample from leaking out of the sample carrier.

As shown in FIG. 14, the bowl 300 is fluidically coupled to the channel 40 at an apex 302 of the bowl 300. The bowl 300 is in the form of a recess from a surface 304 of the sample carrier, and around the perimeter of the bowl 300 where it meets the surface 304 is a protruding edge 306. The protruding edge 306 is proud of the surface 304 into which the bowl 300 is recessed.

As shown in FIG. 15, a cover member 308 is provided. As shown in FIG. 17 the cover member 308 is configured to cover a proximal end of the sample carrier, in particular the area of the sample carrier that includes the sample entry point 38'. The cover member 308 may be slid onto the sample carrier in the direction of the arrows shown in FIG. 17.

As shown in FIG. 18, the cover member 308 can include guide members 310 in order to allow the cover member 308 to be slid along and held in place on the sample carrier.

The guide members 310 can be in the form of first and second rails in the form of recesses in the cover member 308 into which the sample carrier can fit and slide. However, the rails on the cover member in this case create an undercut that a simple up and down tool will not be able to create as is. Accordingly, as shown in FIG. 18a, one option is to create cut outs 314 through a top surface of the cover member 308 to allow the tool to form the undercut. Another option as shown in FIG. 18b is to use two side moves that will move away from the features stopping the tool from clashing with the cover member 308.

The cover member and sample carrier are provided with one or more locking elements 316 for example in the form of protrusions and corresponding detents in order to fix the cover member 308 in position on the sample carrier once they have been slid together.

As can be seen in FIG. 17 the cover member 308 includes a length 318 which is sufficient to cover the area of the sample carrier from the proximal end up to and beyond the sample entry point 38', but which leaves exposure to the detection chamber 42 for operation of the test device. In addition, if a user inputs their sample before placing the sample carrier into a test device, the exposed detection chamber provides a visual indication that the sample has been correctly applied and has entered the detection chamber. The cover member 308 includes a distal wall 320 which is located just proximal of the detection chamber 42 when the cover member 308 is in place on the sample carrier. The distal wall 320 is configured to be substantially flush with a side of a test device when the sample carrier is inserted in a test device in order that after insertion the sample entry point is the only exposed part of the sample carrier. The cover member 308 also includes a sample entry point window 322 disposed to be located to expose the sample entry point 38' when the cover member 308 is in position on the sample carrier. Between the sample entry point window 322 and the distal wall 320, and around the sides of the window 322 except the proximal side, is provided a splash guard 324 which is configured to prevent the sample from reaching any other part of the sample carrier when a sample is being introduced into the sample entry point via the window 322.

In lateral sides of the cover member 308 are provided finger recesses 326 in order to facilitate the insertion of a sample carrier into a test device. At the proximal end of the cover member 308 is provided a closure member 328 which is configured to be movable to expose or close the window 322. The closure member 328 is configured to be movable within a guide 330 provided in the cover member 308, for example, adjacent to the window 322 on the opposite side of the cover member 308 from the splash guard 324. The guide 330 can be recesses formed between the sample carrier and the cover member 308, for example by an edge of the window 322, a surface of the sample carrier adjacent to the cover member 308, and side walls 331. The closure member includes protrusions 332 configured to be guided by the guide 330. The closure member 328 is provided with a thickest section which is thicker than a corresponding section of the guide where it is located in the closed position, thereby to assist with sealing as described below. The closure member 328 in this modification is arranged so that it cannot be completely removed from the cover member 308, in this modification by providing a shoulder 334 at a proximal end of the guide 330 against which the protrusions 332 will abut to prevent their removal from the guide 330. In a further modification, the protrusions can have tapered distal ends as shown in FIG. 22a to assist its initial insertion into the guide 330.

The closure member 328 also includes locking elements to lock the closure member in a position in which it closes the window 322. These locking elements can be in the form of one or more arrowhead protrusions 336 on the closure member 328, in this case two, and corresponding detents 338 on the guide member 330, or vice versa.

In this modification the proximal end of the closure member 328 is flexibly connected by a thin beam 312 to the proximal end of the cover member 308 to prevent their separation but to allow the closure member 328 to be slid to close and expose the window 322. In this way the cover member and closure member can be manufactured as a single moulding. The flexible connection 312 can bias the closure member into an open position so it is effectively spring loaded. In addition, when the closure member is moved to a closed position, it is pushed in and located to seal the entry point, that there is minimal displacement of the sample liquid within the sample carrier (between sample entry point and waste chamber). This prevents pushing material into the waste chamber leaving an air gap (vacuum) behind the liquid and up to the closure member as this would affect the movement of fluids when the storage chambers are burst.

In some embodiments, the locking elements of the closure member are configured so that the closure member cannot be re-opened once closed. This is a safety feature as the sample carrier will contain potentially hazardous sample and is preferably disposable.

The closure member 328 includes a closure protrusion 340 configured so that when the closure member closes the window 322 and the cover member 308 is in place on a sample carrier, the closure protrusion 340 covers the sample entry point 38' and enters the entrance of the bowl 300, forming a seal with the edge 306. As can be seen in FIG. 19, the closure protrusion may correspond with an indentation on the opposite side of the closure member 328. This indentation can be over moulded with a membrane such as TPE, as shown in the inset section of FIG. 19, to improve sealing of the sample entry point as discussed below.

FIG. 19 shows the cover member 308 as it is moulded before the protrusions 332 of the closure member 328 are inserted into and held by the guide 330.

The closure member 328 is operated in the following way.

The cover member 308 is inserted onto a sample carrier until the locking elements 316 co-operate to hold the cover member 308 in place on the sample carrier. At this point the window 322 is open to expose the bowl 300 of the sample entry point 38'. The user then inserts sample into the bowl 300 until the bowl is full or overflowing. Then the user presses on the proximal end of the closure member 328 and slides it within the guide 330 until it closes the window 322 and obstructs the entry to the bowl 300. As shown in FIG. 20, as the closure member is slid over the protruding edge 306 of the bowl, the closure protrusion 340 enters the bowl 300 to provide a seal. In addition, the thickest section of the closure member 328 being thicker than the corresponding section of the guide 330 forces the closure member 328 against the protruding edge 306 thereby to create an airtight seal between the edge 306 and the closure member 328 around the closure protrusion 340. The overmoulded membrane improves the fit and seal. This prevents any sample in the bowl 300 from escaping from the bowl 300 after the closure member 328 has closed the window 322. In addition, because the bowl 300 is the correct volume for the amount of volume of sample that is desired within the sample carrier, closure of the closure member 328 prevents air from entering the sample carrier and cuts off excess sample from the bowl to prevent it from overfilling the sample carrier. This excess sample is prevented from contaminating other areas of the sample carrier by the splash guard 324, and can be easily and conveniently wiped away from the cover member 308 once the closure member 328 has been closed.

Of course, the protrusions and recesses of the guides or guide members described above can be reversed. Furthermore, the edge 306 can be provided on the closure member to press into the surface 304 to form the airtight seal. Furthermore, in other embodiments, the closure member can be provided by adhesive tape, clamps or other mechanisms. However, these lack many of the advantageous features of the closure member described above.

In the embodiment described above, the detection chamber 42 has a rounded shape, such as that shown in FIG. 23. Such a shape could be considered to be a rectangle with rounded corners. However, in modifications, the detection chamber 42' can be configured as shown in FIGS. 24-26. In this modification, the detection chamber 42' is shaped in a substantially hexagonal fashion with the channel 40 and the valve 46 being located at opposite vertices of the hexagonal detection chamber. The detection chamber 42' is symmetrical about a line of symmetry from the channel 40 to the valve 46, with the detection chamber on either side of the line of symmetry forming an isosceles trapezium (isosceles trapezoid in US English). It has been found that the hexagonal shape for the detection chamber 42' is particularly effective in preventing air bubbles from becoming caught in the detection chamber.

As shown in FIG. 23, the detection chamber can include pillars 342 to increase the surface area available for dried down reagents, thereby to enhance the mixing of the sample for example with carrier and label elements. The pillars can also smooth fluid flow.

Exemplary capacities of individual features in a sample carrier arranged such as that shown in FIG. 23 can be as follows. The capacity of the first storage chamber 50 can be 39 µl pure microstructure, or 50 µl including adhesive foil thickness. The capacity of the channel 54 leading from the first storage chamber 50 to the channel 40 can be 23.2 µl pure microstructure. The capacity of the channel 56 leading from the second storage chamber to the channel 40 can be 8.4 µl pure microstructure. The capacity of the detection chamber 42 can be 40.8 µl pure microstructure or 52.9 µl including adhesive foil thickness. The capacity of the waste chamber 44 can be 297.7 µl pure microstructure or 342.1 µl including adhesive foil thickness.

In a modification, the capacity of channel 54 can be 8.4 µl as per channel 56.

FIG. 27 shows a cross section of a test device 80 according to an embodiment of the invention. FIG. 28 shows a side cross-sectional view also including a spring chamber 105 which is for rig force testing and not needed in a final product.

The test device 80 includes a holder 82 with an opening in a proximal end of the device which can receive a sample carrier such as a sample carrier 30 described above. The holder 82 is configured so that as a sample carrier is inserted into the holder 82, the test device does not cause compression of any compressible chambers which may be located on the sample carrier.

In the holder there is provided a connector to connect to detection terminals, such as electrodes 60, of a sample carrier, such as by connecting to connector 61, to allow readings to be taken. There can also be provided a sample carrier retaining element 120 for interlocking with a detent on a sample carrier.

In the depicted embodiment, the test device 80 includes a magnet arrangement 84. However, the magnet arrangement is for holding magnetic carrier elements in a sample carrier and may be omitted from test devices for sample carriers for other kinds of test. The magnet arrangement 84 includes a solenoid 86 coupled to an arm 88 the end of which is located at a region of the holder 82 adjacent to where the detection chamber 42 of the sample carrier 30 would be located when the sample carrier 30 is held within the holder 82.

In a modification, the solenoid 86 is replaced with a linear motor which is operable to move the arm 88, and at the end of the arm 88 which is located at a region of the holder 82 adjacent to where the detection chamber 42 of the sample carrier 30 would be located, is provided a permanent magnet. The motor of the modified magnet arrangement 84' is operable to move the permanent magnet in a lateral direction, in other words, substantially perpendicular to the proximal-distal direction, in order to move the permanent magnet back and forth across the detection chamber 42 of a sample carrier 30. This can be used to aid the mixing of the carrier elements and label elements during the incubation stage of the exemplary assay method described above. In addition, the motor of the modified magnet arrangement 84' is operable to hold the permanent magnet in a position adjacent to the detection chamber 42 in order to hold the carrier elements in position during the separation phase. Preferably, he motor of the modified magnet arrangement 84' is operable to position the permanent magnet adjacent to the detection chamber 42 before any of the compressible storage chambers of the sample carrier are compressed.

The test device 80 also includes an actuator. The actuator includes a first pivotable member 90 and a second pivotable member 92. Each of the first and second pivotable members includes a chamber actuation section 94, typically a blister popping ramp or finger, which is disposed on a first side of the pivotable member, wherein the first side faces a sample carrier in the holder 82. The chamber actuation section is located on a first side of the pivotable member adjacent to a location at which one of the compressible storage chambers 50, 52 of the sample carrier 30 is located when the sample carrier 30 is held in the holder 82. Both of the first and second pivotable members 90, 92 are pivotable about a pivot 96. In this embodiment, the pivot 96 is located between a proximal and a distal end of each pivotable member. The first and second pivotable members 90, 92 are each separately pivotable between a non-compressing position in which the pivotable member does not compress a respective chamber of a sample carrier held in the holder, and a compressing position in which the chamber actuation section 94 compresses the respective chamber of the sample carrier 30. In embodiments, in the non-compressing position, a clearance is left between a volume that would be occupied by a compressible storage chamber and the respective chamber actuation section. The first and second pivotable members are configured so that, unless actuated by a pivotable actuation member described below, they are in the non-compressing position.

In the embodiment of FIGS. 34-36 and 38-39, the positions of the first and second pivotable members have been interchanged.

In other embodiments there may be more or fewer than two pivotable members. However, there should be a chamber actuation section for each compressible chamber on a corresponding sample carrier. In some embodiments, multiple chamber actuation sections can be provided on one pivotable member.

The actuator includes a linear motor 98 operable to advance, for example by way of a linear piston, a pivot actuation member 100 proximally towards distal ends of the first and second pivotable members. The linear motor 98 can be the same linear motor as operates the magnet arrangement 84'.

The pivot actuation member is arranged so as to provide a first pivot actuation member 102 which is longer than a second pivot actuation member 104. The first pivot actuation member 102 is configured so that as it is advanced by the linear motor 98 it contacts the first side of the first pivotable member distally of the pivot 96, thereby pivoting the first pivotable member 90 into the compressing position. Correspondingly, the second pivot actuation member 104 is configured so that as it is advanced by the linear motor 98, it contacts the first side of the second pivotable member 92 distally of the pivot 96, thereby pivoting the second pivotable member into the compressing position.

The relative lengths for the first pivot actuation member 102 and the second pivot actuation member 104 are arranged so that as the linear motor 98 advances them, there will be a predetermined period between pivoting the first pivotable member into the compressing position and pivoting the second pivotable member into the compressing position. This predetermined period can be selected on the basis of the test to be performed, such as to allow a suitable time for a wash solution to wash a detection chamber of a sample carrier.

In order to smooth the movement of the first and second pivot actuation members 102, 104 against the pivotable members 90, 92, the pivot actuation members 102, 104 can be provided with bearings 106. Furthermore, the first and second pivotable members 102, 104 can be provided with CAM surface against which the bearings 106 contact as the pivot actuation members are advanced.

The CAM surfaces of the pivotable members can be configured so that in the non-compressing position, the CAM surfaces are inclined with respect to the proximal direction. Typically, this is by providing the distal end of each of the pivotable members as a wedge shape as depicted.

This can mean that as the pivot actuation members are advanced proximally, the angles at which the pivotable members are pivoted are increased only gradually. This can provide for a smooth movement of the chamber actuation sections onto chambers of a sample carrier.

The compression pressure on the chambers of the sample carrier can be selected by appropriately configuring the angle of inclination of the CAM surface of the respective pivotable member. For example, if for every 3 mm in the proximal direction, the inclination of the CAM surface results in it also extending 1 mm perpendicular to that direction, this would create a force from the respective chamber actuation section on a chamber of a sample carrier which is 3× greater than the linear force of the pivot actuation member which is advantageous.

The pivot actuation members are of sufficient length so that once the respective pivotable member has been pivoted to the compression position, further advancement of the pivot actuation member does not release the pivotable member to return to the non-compression position. This is important as the chambers of the sample carrier need to be held down in a stationary position since removal of pressure would cause the chamber to slightly re-inflate thereby sucking fluid back.

In an alternative embodiment, instead of the first pivot actuation member 102 being longer than the second pivot actuation member 104, the first pivotable member 90 can extend distally of the second pivotable member 92.

The test device 80 can also be provided with a scanner 108 for scanning barcodes.

The elements of the test device 80 can all be provided on a printed circuit board 110 which is powered by a battery 112.

In addition, as shown for example in FIG. 29, the test device 80 can be provided with a screen 114 and an input component 116. The test device 80 can also be provided with a processor programmed to perform an assay. A schematic system diagram is shown in FIG. 51. The processor can control the power and movement of the linear motor. The linear motor and/or processor may include a feedback mechanism so that the linear motor and/or processor can detect if an actuation command has not been fully executed and can adjust the power or speed or other parameter of the linear motor in order to complete the actuation command.

The test device can be operable to detect the presence of a sample in a sample carrier, for example by operation of the detection terminals 60, and it can be operable to detect errors in a test for example from the electrochemical performance and signals received from the detection terminals it can be operable to determine whether a test was performed within predetermined criteria and to provide an error message if not.

The test device can be enclosed within a casing 118.

The test device 80 can be operated as follows.

The scanner 108 can be used to scan a barcode on a sample carrier. The test device will show on the screen information derived from the scanned barcode to allow a user to determine whether he/she has the correct sample carrier for the test he/she wishes to perform.

A sample carrier 30, such as described above, can be inserted into the holder 82 until the sample carrier retaining element 120 interlocks with the detent 62 on the sample carrier. Once the user has inserted a sample into and sealed the sample entry point 38, the user can indicate to the test device using the input component 116 that the sample has been entered or the test device can detect the presence of the sample. The processor of the test device 80 waits for a predetermined delay in order to allow the sample to incubate in the detection chamber 42 of the sample carrier 30. It can during this time operate the magnet arrangement 84 to provide a switching magnetic or electromagnetic field in a programmed sequence to the detection chamber to aid mixing by moving magnetic particles.

In the modification in which the magnet arrangement 84' includes a movable permanent magnet, the magnet can be moved laterally across the detection chamber to assist mixing as shown in FIG. 52 in which the arrow indicates the movement of the magnet across the detection chamber. As a sample carrier is entered into the test device the default position is for the magnet to be moved to the furthest away point of its movement carriage which is away from the detection chamber. This allows the re-suspension of the dried down materials (magnetic carrier elements and label elements) to occur otherwise the magnetic carrier elements would be held down on a surface of the sample chamber. This also allows them to drop from an upper surface of the sample carrier and in the process mix with the sample. Then the magnet is moved rapidly across the detection chamber to move the magnetic particles and cause turbulence within the detection chamber. This turbulence causes/enhances the re-suspension and causes mixing of the sample with the reagents to improve reaction. The mixing is then stopped and the incubation continues (time for each of these mixing processes is controlled from the test device and there can be pulsed or multiple mixing steps within the overall incubation period).

If a magnetic/electromagnetic field has been used to aid mixing, the field is switched off, for example by moving the permanent magnet away for the detection chamber for a predetermined delay to allow complexes to form in the detection chamber.

After the predetermined delay, the processor of the test device 80 operates the magnetic arrangement 84 to apply an electromagnetic/magnetic field to the detection chamber 42. The processor of the test device 80 is then configured to operate the linear motor 98 to advance the first and second pivot actuation members 102, 104 at a predetermined constant speed. As the bearings 106 of the first pivot actuation member 102 encounter the CAM surface of the first pivotable member 90, the first pivot actuation member 102 forces the first pivotable member 90 to pivot so that its chamber actuation section 94 compresses the first storage chamber 50 of the sample carrier 30.

Owing to the different lengths of the first and second pivot actuation members 102, 104, as the linear motor 98 continues to advance the first and second pivot actuation members 102, 104 at a constant speed, the bearings 106 of the second pivot actuation member 104 encounter the CAM surface of the second pivotable member 92 after a predetermined time and cause this to pivot about the pivot 96 so that the chamber actuation section 94 of the second pivotable member 92 compresses the second storage chamber 52 of the sample carrier 30. However, the first pivotable member is maintained in a compressing position to prevent fluid from being sucked back into the first storage chamber and allowing air into the sample carrier.

In some embodiments, the processor of the test device can be configured to pause the linear motor between pivoting the first pivotable member and pivoting the second pivotable member in order to increase the predetermined time. Additionally, this pause can be used to provide the predetermined time between pivoting the first and second pivtoable members instead of providing the first and second pivot actuation members with different lengths.

The test device 80 is then configured to use the connector to operate the electrodes 60 to take one or more readings from the detection chamber 42 of the sample carrier 30.

The test device 80 is then configured to perform an appropriate analysis of the readings from the electrodes 60 and to provide the results on the screen 114 for example by way of a measurement or a diagnosis.

In terms of defined movements of the first and second pivot actuation members, an example of a program to be run on the processor for operating the pivot actuation members is as follows:

1. Move forward full speed 5-6 mm.
2. Pause for 2 seconds.
3. Move forward ¼ speed to 10-12 mm.
4. Pause 3-4 seconds.
5. Move forward full speed to 15-16 mm.
6. Pause for 2 seconds.
7. Move forward ¼ speed to 20 mm.
8. Pause 3-4 seconds.
9. Stop.
10. Begin read sequence.

Particular advantages of the test device described above is that it can compress compressible chambers in a predetermined controlled manner, providing a precisely controlled amount of force at a precisely controlled time during a test. This is beneficial in order to prevent solutions or other fluids being pressed around the sample carrier at too high a pressure which might damage the sample carrier or force important solution to be undesirably pushed into the waste chamber. It can also prevent the sample carrier being below pressure with a consequential risk of air bubbles in the system.

Air bubbles in the sample carrier can interfere with a test. They can be located near to a detection chamber, which can cause erroneous test readings. Also, they can take up space within the sample carrier which should ideally be filled with sample. This can reduce the amount of sample in the sample carrier, potentially reducing the effectiveness of the test. As described above, advantageous configurations of the detection chamber can reduce the likelihood of air bubbles becoming trapped. In addition, the test device, by preventing reinflation of the compressible storage chambers once they have been compressed, is able to prevent fluid from being sucked back away from the detection chamber, which may in turn draw air into the detection chamber. It is also able to prevent compressible storage chambers becoming inflated with air which may then diffuse or be drawn into the detection chamber.

Although the pivotable members described herein are able to combine maintaining compression of the compressible storage chambers with a precise and effective compression process, compression of the compressible storage chambers can be maintained in other ways. For example, the actuator can include one or more presses for pressing on compressible storage chambers of a sample carrier in order effect their compression. This or these presses can for example be operated by a linear motor which in turn is controlled by the processor. The processor can be programmed to maintain pressure on the press or presses after compression of each compressible storage chamber to prevent reinflation.

Although embodiments described above discuss compressible storage chambers and mechanisms for compressing them, it is to be appreciated that in a modification, the storage chambers can be pressurised and the test device mechanisms can depressurise them, for example by bursting them, whereupon they will discharge under their own pressure. However, the test device preferably includes mechanisms for preventing their reinflation, for example by maintaining them in their compressed or depressurised state.

Another example of a sample carrier that can be used with a test device according to an embodiment of the invention is shown in FIG. 44. The sample carrier shown in FIG. 44 corresponds to the sample carrier 30 shown in FIG. 6 except that the centres of the first and second storage chambers are level with the sample entry point rather than being distal of the detection chamber. Accordingly, this example is less preferred since it difficult to apply a sample to the sample carrier while the sample carrier is held within a holder of the test device.

Another embodiment of a test device is shown in FIGS. 47 to 50. The test device shown in FIGS. 47 to 50 corresponds to the test device shown in FIG. 27 except as described below.

In the embodiment of FIGS. 47 to 50, the actuator includes first and second pivotable members 190, 192. At a distal end of each of the pivtoable members 190, 192 is provided a chamber actuation section as described above. The chamber actuation section is arranged on a first side of the pivotable member, wherein the first side faces a sample carrier in the holder. On a second side of each of the pivotable members 190, 192, which is a side opposite from the first side, is provided a protrusion 200. The protrusions and chamber actuation sections are both proximal of the pivot. The protrusions 200 are arranged on the second side with a distally facing inclined surface. The protrusion 200 of the first pivotable member 190 extends distally of the protrusion of the second pivotable member 192. However, the proximal ends of the protrusions are substantially level.

The actuator includes first and second channels 210, 220 which serve to guide a pivot actuation member 230 along the second side of the first and second pivotable members towards the protrusions 200.

In use, the linear motor 98 advances the pivot actuation member 230 proximally along the second side of the first and second pivotable members 190, 192. In one embodiment, the linear motor delivers 27N. The pivot actuation member will encounter the protrusion 200 of the first pivtoable member 190 before the protrusion of the second pivotable member owing to the first pivotable member 190 extending distally of the second pivotable member.

As the pivot actuation member encounters the inclined distal surface of the protrusion 200 of the first pivotable member 190, the inclined surface of the protrusion 200 will convert the proximal motion of the pivot actuation member into a force pressing the first pivotable member 190, and thereby the chamber actuation section of the first pivotable member 190, towards a first storage chamber of the sample carrier held in the holder, thereby compressing that chamber.

As the linear motor 98 continues to advance the pivot actuation member, the pivot actuation member will hold the first pivotable member 190 in the compressing position owing to the proximal extent of the protrusion of the first pivotable member 190. After a predetermined time governed by the amount the distal surface of the protrusion of the first pivotable member extends distally of the distal surface of the protrusion of the second pivotable member 192, the pivot actuation member will encounter the inclined distal surface of the protrusion 200 of the second pivotable member. This will work to cause the chamber actuation section of the second pivotable member to compress a second storage chamber on a sample carrier in the holder in an analogous manner to that described in respect of the first pivotable member.

In a modification, the test device and/or sample carrier can be provided with a piezoelectric mechanism operable to shake or vibrate the detection chamber and optionally to heat the detection chamber during the incubation stage to aid mixing of the sample, carrier elements and label elements.

It is to be appreciated that certain embodiments of the invention as discussed herein may be incorporated as code (e.g., a software algorithm or program) residing in firmware and/or on computer useable medium having control logic for enabling execution on a computer system having a computer processor. Such a computer system typically includes memory storage configured to provide output from execution of the code which configures a processor in accordance with the execution. The code can be arranged as firmware or software, and can be organized as a set of modules such as discrete code modules, function calls, procedure calls or objects in an object-oriented programming environment. If implemented using modules, the code can comprise a single module or a plurality of modules that operate in cooperation with one another.

Optional embodiments of the invention can be understood as including the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although illustrated embodiments of the present invention have been described, it should be understood that various changes, substitutions, and alterations can be made by one of ordinary skill in the art without departing from the present invention which is defined by the recitations in the claims below and equivalents thereof.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in British patent application number 1217390.2, from which this application claims priority, and in the abstract accompanying this application are incorporated herein by reference.

The invention claimed is:

1. A test device for testing for the presence of a substance in a sample held on a sample carrier that includes a chamber or a plurality of chambers; the test device including a holder for holding the sample carrier, and an actuator for compressing the chamber or the plurality of chambers, wherein the test device is part of a test to perform at least one interaction with the sample carrier subsequently to compressing the chamber or the plurality of chambers; the actuator maintaining compression of the chamber or the plurality of chambers after compression, until the or each of the at least one interaction has been performed,
wherein the actuator includes a first pivotable member including a first chamber actuation section pivotable into a first chamber location, wherein the first chamber location is a location at which a chamber of the sample carrier is located when the sample carrier is held in the holder; and a driver operable to pivot the first pivotable member to cause the first chamber actuation section to be pivoted into the first chamber location thereby to compress the chamber in the first chamber location;
wherein the driver includes a motor operable to advance a pivot actuation member, wherein the first pivotable member includes a contact surface against which the pivot actuation member impacts, as the pivot actuation member advances, to cause the first pivotable member to pivot to cause the first chamber actuation section to be pivoted into the first chamber location; wherein the pivot actuation member has a length to maintain the first pivotable member in a pivoted position with the first chamber actuation section in the first chamber location as the pivot actuation member advances subsequently to the first pivotable member being pivoted.

2. The test device according to claim 1 wherein the actuator is operable to burst the chamber or the plurality of chambers.

3. The test device according to claim 1, wherein the first pivotable member includes a second chamber actuation section pivotable into a second chamber location, wherein the second chamber location is a location at which a chamber of the sample carrier is located when the sample carrier is held in the holder; the driver being operable to pivot the first pivotable member to cause the second chamber actuation section to be pivoted into the second chamber location thereby to compress the chamber in the second chamber location.

4. The test device according to claim 3, wherein the driver is operable to pivot the first pivotable member to cause the first chamber actuation section to be pivoted into the first chamber location a predetermined period of time before pivoting the second chamber actuation section into the second chamber location.

5. The test device according to claim 1, wherein the actuator includes a second pivotable member including a second chamber actuation section pivotable into a second chamber location, wherein the second chamber location is a location at which a chamber of the sample carrier is located when the sample carrier is held in the holder; the driver being operable to pivot the second pivotable member to cause the second chamber actuation section to be pivoted into the second chamber location thereby to compress the chamber in the second chamber location.

6. The test device according to claim 5, wherein the second pivotable member includes a contact surface against which the pivot actuation member impacts, as the pivot actuation member advances, to cause the second pivotable member to pivot to cause the second chamber actuation section to be pivoted into the second chamber location; wherein the pivot actuation member has a length to maintain the second pivotable member in a pivoted position with the second chamber actuation section in the second chamber location as the pivot actuation member advances subsequently to the second pivotable member being pivoted.

7. The test device according to claim 1, wherein the motor is a linear motor.

8. The test device according to claim 1, wherein the first pivotable member includes a pivot between the contact surface of the first pivotable member and the first chamber actuation section.

9. The test device according to claim 8, wherein the contact surface of the first pivotable member is configured to be inclined with respect to a direction of movement of the pivot actuation member or the contact surface of the second pivotable member is configured to be inclined with respect to a direction of movement of the pivot actuation member.

10. A method of performing a test for a substance in a sample held in a sample carrier, including:

operating an actuator to compress a fluid-filled storage chamber of the sample carrier or a plurality of fluid-filled storage chambers of the sample carrier to cause fluid from the storage chamber or from the plurality of storage chambers to be moved;

operating the actuator to prevent reinflation of the storage chamber or of the plurality of storage chambers;

operating a detector to interact with fluid in a detection chamber to test for the substance; wherein performing the test includes performing at least one interaction with the sample carrier subsequently to compressing the storage chamber or the plurality of storage chambers; wherein operating the actuator to prevent reinflation of the storage chamber or of the plurality of storage chambers includes maintaining compression of the storage chamber or of the plurality of storage chambers after compression until the or each of the at least one interaction has been performed, wherein the actuator includes a first pivotable member including a first chamber actuation section pivotable into a first location, the first location being a location of the storage chamber or of a first chamber of the plurality of storage chambers; the method including operating a driver to pivot the first pivotable member to cause the first chamber actuation section to be pivoted into the first location thereby to compress the storage chamber or the first chamber of the plurality of storage chambers;

wherein the driver includes a motor operable to advance a pivot actuation member, wherein operating the driver to pivot the first pivotable member includes operating the motor to advance the pivot actuation member to pivot the first pivotable member to cause the first chamber actuation section to be pivoted into the first location.

11. The method according to claim 10, wherein operating an actuator to compress a plurality of fluid-filled storage chambers of the sample carrier includes operating the actuator to compress the plurality of storage chambers in a controlled sequence; or wherein the method includes implementing a predetermined delay before operating the actuator to compress the storage chamber of the sample carrier or the plurality of storage chambers of the sample carrier wherein the predetermined delay is started in response to performance of the test beginning.

12. The method according to claim 11, wherein the predetermined delay is started in response to insertion of the sample carrier into a holder, in response to a command to begin performance of the test, or in response to a sample sensor sensing the presence of the sample in the sample carrier.

13. The method according to claim 10, wherein the first pivotable member includes a second chamber actuation section pivotable into a second location, the second location being a location of a second chamber of the plurality of storage chambers; the method including operating the driver to pivot the first pivotable member to cause the second chamber actuation section to be pivoted into the second location thereby to compress the storage chamber in the second chamber location.

14. The method according to claim 13, the method including operating the driver to pivot the first pivotable member to cause the first chamber actuation section to be pivoted into the first location a predetermined period of time before pivoting the second chamber actuation section into the second location.

15. The method according to claim 10, wherein the actuator includes a second pivotable member including a second chamber actuation section pivotable into a second location, the second location being a location of a second chamber of the plurality of storage chambers; the method including operating the driver to pivot the second pivotable member to cause the second chamber actuation section to be pivoted into the second location thereby to compress the storage chamber in the second location.

16. The method according to claim 15, the method including operating the driver to pivot the first pivotable member before the second pivotable member.

17. The method according to claim 15, including, subsequently to pivoting the first pivotable member, operating the motor to advance the pivot actuation member to pivot the second pivotable member to cause the second chamber actuation section to be pivoted into the second location while maintaining the first chamber actuation section in the first location to prevent reinflation of the first chamber.

18. The method according to claim 10, wherein operating the motor to advance the pivot actuation member includes operating the motor to advance the pivot actuation member linearly.

19. A processor for a test device, the processor being programmed with program code to perform the following method:

operating an actuator to compress a fluid-filled storage chamber of the sample carrier or a plurality of fluid-filled storage chambers of the sample carrier to cause fluid from the storage chamber or from the plurality of storage chambers to be moved;

operating the actuator to prevent reinflation of the storage chamber or of the plurality of storage chambers;

operating a detector to interact with fluid in a detection chamber to test for the substance; wherein performing the test includes performing at least one interaction with the sample carrier subsequently to compressing the storage chamber or the plurality of storage chambers; wherein operating the actuator to prevent reinflation of the storage chamber or of the plurality of storage chambers includes maintaining compression of the storage chamber or of the plurality of storage chambers after compression until the or each of the at least one interaction has been performed;

wherein the actuator includes a first pivotable member including a first chamber actuation section pivotable into a first location, the first location being a location of the storage chamber or of a first chamber of the plurality of storage chambers; the method including operating a driver to pivot the first pivotable member to cause the first chamber actuation section to be pivoted into the first location thereby to compress the storage chamber or the first chamber of the plurality of storage chambers;

wherein the driver includes a motor operable to advance a pivot actuation member, wherein operating the driver to pivot the first pivotable member includes operating the motor to advance the pivot actuation member to pivot the first pivotable member to cause the first chamber actuation section to be pivoted into the first location.

\* \* \* \* \*